US009452017B2

(12) United States Patent
Chang et al.

(10) Patent No.: US 9,452,017 B2
(45) Date of Patent: Sep. 27, 2016

(54) MULTI-ELECTRODE CATHETER ASSEMBLIES FOR RENAL NEUROMODULATION AND ASSOCIATED SYSTEMS AND METHODS

(71) Applicant: Medtronic Ardian Luxembourg S.a.r.l., Luxembourg (LU)

(72) Inventors: William W. Chang, Santa Rosa, CA (US); Justin Goshgarian, Santa Rosa, CA (US); Kevin Michael Mauch, Windsor, CA (US); Leonila Rivera, Windsor, CA (US); Sukyoung Shin, Santa Rosa, CA (US); Don H. Tran, Novato, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 14/824,155

(22) Filed: Aug. 12, 2015

(65) Prior Publication Data

US 2016/0066988 A1 Mar. 10, 2016

Related U.S. Application Data

(63) Continuation of application No. 14/511,078, filed on Oct. 9, 2014, now Pat. No. 9,138,292, which is a continuation of application No. 13/793,647, filed on Mar. 11, 2013, now Pat. No. 8,888,773.

(60) Provisional application No. 61/646,218, filed on May 11, 2012.

(51) Int. Cl.
*A61B 18/18* (2006.01)
*A61B 18/14* (2006.01)
(Continued)

(52) U.S. Cl.
CPC ....... *A61B 18/1492* (2013.01); *A61B 18/1206* (2013.01); *A61M 25/0102* (2013.01);
(Continued)

(58) Field of Classification Search
CPC ............... A61B 18/1492; A61B 2018/00005; A61B 2018/00404; A61B 2018/00577; A61B 2018/1465; A61B 2018/1435; A61B 2018/1475
See application file for complete search history.

(56) References Cited

U.S. PATENT DOCUMENTS 3,935,348 A    1/1976   Smith
4,154,246 A    5/1979   LeVeen
(Continued)

FOREIGN PATENT DOCUMENTS

AU    2011239313    5/2012
AU    2011239316    5/2012
(Continued)

OTHER PUBLICATIONS

Allen, E.V., Sympathectomy for essential hypertension, Circulation, 1952, 6:131-140.
(Continued)

*Primary Examiner* — Robert N Wieland

(57) ABSTRACT

Catheter apparatuses, systems, and methods for achieving renal neuromodulation by intravascular access are disclosed herein. One aspect of the present technology, for example, is directed to a treatment device having a multi-electrode array configured to be delivered to a renal blood vessel. The array is selectively transformable between a delivery or low-profile state (e.g., a generally straight shape) and a deployed state (e.g., a radially expanded, generally spiral/helical shape). The multi-electrode array is sized and shaped so that the electrodes or energy delivery elements contact an interior wall of the renal blood vessel when the array is in the deployed (e.g., spiral/helical) state. The electrodes or energy delivery elements are configured for direct and/or indirect application of thermal and/or electrical energy to heat or otherwise electrically modulate neural fibers that contribute to renal function.

24 Claims, 5 Drawing Sheets

(51) Int. Cl.
*A61M 25/01* (2006.01)
*A61B 18/12* (2006.01)
*A61B 18/00* (2006.01)
*A61M 25/09* (2006.01)

(52) U.S. Cl.
CPC ..... *A61M25/09* (2013.01); *A61B 2018/00059* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/1435* (2013.01); *A61B 2018/1465* (2013.01); *A61B 2018/1467* (2013.01); *A61M 2025/0915* (2013.01)

(56) References Cited

U.S. PATENT DOCUMENTS

| | | |
|---|---|---|
| 4,169,464 A | 10/1979 | Obrez |
| 4,419,819 A | 12/1983 | Dickhudt et al. |
| 4,488,561 A | 12/1984 | Doring |
| 4,602,624 A | 7/1986 | Naples et al. |
| 4,649,936 A | 3/1987 | Ungar et al. |
| 4,660,571 A | 4/1987 | Hess et al. |
| 4,706,671 A | 11/1987 | Weinrib |
| 4,709,698 A | 12/1987 | Johnston et al. |
| 4,764,504 A | 8/1988 | Johnson et al. |
| 4,781,682 A | 11/1988 | Patel |
| 4,796,643 A | 1/1989 | Nakazawa et al. |
| 4,819,661 A | 4/1989 | Heil, Jr. et al. |
| 4,834,724 A | 5/1989 | Geiss et al. |
| 4,860,769 A | 8/1989 | Fogarty et al. |
| 4,890,623 A | 1/1990 | Cook et al. |
| 4,920,979 A | 5/1990 | Bullara |
| 4,921,484 A | 5/1990 | Hillstead |
| 4,957,118 A | 9/1990 | Erlebacher |
| 4,961,377 A | 10/1990 | Bando et al. |
| 4,976,711 A | 12/1990 | Parins et al. |
| 4,995,868 A | 2/1991 | Brazier |
| 5,002,067 A | 3/1991 | Berthelsen et al. |
| 5,011,488 A | 4/1991 | Ginsburg |
| 5,016,808 A | 5/1991 | Heil, Jr. et al. |
| 5,052,998 A | 10/1991 | Zimmon |
| 5,054,501 A | 10/1991 | Chuttani et al. |
| 5,071,407 A | 12/1991 | Termin et al. |
| 5,071,424 A | 12/1991 | Reger |
| 5,133,365 A | 7/1992 | Heil, Jr. et al. |
| 5,156,151 A | 10/1992 | Imran |
| 5,156,610 A | 10/1992 | Reger |
| 5,158,564 A | 10/1992 | Schnepp-Pesch et al. |
| 5,163,928 A | 11/1992 | Hobbs et al. |
| 5,188,602 A | 2/1993 | Nichols |
| 5,188,619 A | 2/1993 | Myers |
| 5,209,723 A | 5/1993 | Twardowski et al. |
| 5,211,651 A | 5/1993 | Reger et al. |
| 5,228,442 A | 7/1993 | Imran |
| 5,239,999 A | 8/1993 | Imran |
| 5,249,585 A | 10/1993 | Turner et al. |
| 5,263,492 A | 11/1993 | Voyce |
| 5,263,493 A | 11/1993 | Avitall |
| 5,279,299 A | 1/1994 | Imran |
| 5,296,510 A | 3/1994 | Yamada et al. |
| 5,300,068 A | 4/1994 | Rosar et al. |
| 5,300,099 A | 4/1994 | Rudie |
| 5,308,323 A | 5/1994 | Sogawa et al. |
| 5,318,525 A | 6/1994 | West et al. |
| 5,324,284 A | 6/1994 | Imran |
| 5,327,905 A | 7/1994 | Avitall |
| 5,345,031 A | 9/1994 | Schwartz et al. |
| 5,345,936 A | 9/1994 | Pomeranz et al. |
| 5,354,297 A | 10/1994 | Avitall |
| 5,358,514 A | 10/1994 | Schulman et al. |
| 5,365,926 A | 11/1994 | Desai |
| 5,368,591 A | 11/1994 | Lennox et al. |
| 5,383,856 A | 1/1995 | Bersin |
| 5,387,233 A | 2/1995 | Alferness et al. |
| 5,397,304 A | 3/1995 | Truckai |
| 5,397,339 A | 3/1995 | Desai |
| 5,405,374 A | 4/1995 | Stein |
| 5,411,546 A | 5/1995 | Bowald et al. |
| 5,423,744 A | 6/1995 | Gencheff et al. |
| 5,425,364 A | 6/1995 | Imran |
| 5,427,118 A | 6/1995 | Nita et al. |
| 5,462,545 A | 10/1995 | Wang et al. |
| 5,476,495 A | 12/1995 | Kordis et al. |
| 5,476,498 A | 12/1995 | Ayers |
| 5,484,400 A | 1/1996 | Edwards et al. |
| 5,487,385 A | 1/1996 | Avitall |
| 5,487,757 A | 1/1996 | Truckai et al. |
| 5,497,774 A | 3/1996 | Swartz et al. |
| 5,505,201 A | 4/1996 | Grill, Jr. et al. |
| 5,507,743 A | 4/1996 | Edwards et al. |
| 5,509,909 A | 4/1996 | Moy |
| 5,523,092 A | 6/1996 | Hanson et al. |
| 5,529,820 A | 6/1996 | Nomi et al. |
| 5,545,193 A | 8/1996 | Fleischman et al. |
| 5,545,200 A | 8/1996 | West et al. |
| 5,545,475 A | 8/1996 | Korleski |
| 5,549,661 A | 8/1996 | Kordis et al. |
| 5,564,440 A | 10/1996 | Swartz et al. |
| 5,571,147 A | 11/1996 | Sluijter et al. |
| 5,575,766 A | 11/1996 | Swartz et al. |
| 5,575,810 A | 11/1996 | Swanson et al. |
| 5,582,609 A | 12/1996 | Swanson et al. |
| 5,588,964 A | 12/1996 | Imran et al. |
| 5,591,132 A | 1/1997 | Carrie |
| 5,599,345 A | 2/1997 | Edwards et al. |
| 5,609,151 A | 3/1997 | Mulier et al. |
| 5,617,854 A | 4/1997 | Munsif |
| 5,626,576 A | 5/1997 | Janssen |
| 5,628,775 A | 5/1997 | Jackson et al. |
| 5,636,634 A | 6/1997 | Kordis et al. |
| 5,637,090 A | 6/1997 | McGee et al. |
| 5,642,736 A | 7/1997 | Avitall |
| 5,672,174 A | 9/1997 | Gough et al. |
| 5,676,662 A | 10/1997 | Fleischhacker et al. |
| 5,678,296 A | 10/1997 | Fleischhacker et al. |
| 5,680,860 A | 10/1997 | Imran |
| 5,681,280 A | 10/1997 | Rusk et al. |
| 5,687,723 A | 11/1997 | Avitall |
| 5,688,266 A | 11/1997 | Edwards et al. |
| 5,690,611 A | 11/1997 | Swartz et al. |
| 5,693,082 A | 12/1997 | Warner et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,715,818 A | 2/1998 | Swartz et al. |
| 5,716,410 A | 2/1998 | Wang et al. |
| 5,722,401 A | 3/1998 | Pietroski et al. |
| 5,725,512 A | 3/1998 | Swartz et al. |
| 5,727,555 A | 3/1998 | Chait |
| 5,730,127 A | 3/1998 | Avitall |
| 5,730,741 A | 3/1998 | Horzewski et al. |
| 5,755,760 A | 5/1998 | Maguire et al. |
| 5,755,761 A | 5/1998 | Obino |
| 5,772,590 A | 6/1998 | Webster, Jr. |
| 5,800,494 A | 9/1998 | Campbell et al. |
| 5,807,395 A | 9/1998 | Mulier et al. |
| 5,814,028 A | 9/1998 | Swartz et al. |
| 5,823,955 A | 10/1998 | Kuck et al. |
| 5,827,242 A | 10/1998 | Follmer et al. |
| 5,827,268 A | 10/1998 | Laufer |
| 5,842,984 A | 12/1998 | Avitall |
| 5,846,355 A | 12/1998 | Spencer et al. |
| 5,860,920 A | 1/1999 | McGee et al. |
| 5,860,974 A | 1/1999 | Abele |
| 5,865,787 A | 2/1999 | Shapland et al. |
| 5,865,815 A | 2/1999 | Tihon |
| 5,871,523 A | 2/1999 | Fleischman et al. |
| 5,871,531 A | 2/1999 | Struble |
| 5,873,865 A | 2/1999 | Horzewski et al. |
| 5,879,295 A | 3/1999 | Li et al. |
| 5,882,346 A | 3/1999 | Pomeranz et al. |

(56) References Cited

U.S. PATENT DOCUMENTS

| | | |
|---|---|---|
| 5,891,114 A | 4/1999 | Chien et al. |
| 5,893,885 A | 4/1999 | Webster et al. |
| 5,910,129 A | 6/1999 | Koblish et al. |
| 5,931,848 A | 8/1999 | Saadat |
| 5,938,694 A | 8/1999 | Jaraczewski et al. |
| 5,941,823 A | 8/1999 | Chait |
| 5,944,710 A | 8/1999 | Dev et al. |
| 5,951,471 A | 9/1999 | de la Rama et al. |
| 5,951,494 A | 9/1999 | Wang et al. |
| 5,951,539 A | 9/1999 | Nita et al. |
| 5,954,719 A | 9/1999 | Chen et al. |
| 5,957,961 A | 9/1999 | Maguire et al. |
| 5,968,085 A | 10/1999 | Morris et al. |
| 5,972,019 A | 10/1999 | Engelson et al. |
| 5,972,026 A | 10/1999 | Laufer et al. |
| 5,980,516 A | 11/1999 | Mulier et al. |
| 5,983,141 A | 11/1999 | Sluijter et al. |
| 5,993,462 A | 11/1999 | Pomeranz et al. |
| 5,997,526 A | 12/1999 | Giba et al. |
| 6,004,269 A | 12/1999 | Crowley et al. |
| 6,004,316 A | 12/1999 | Laufer |
| 6,004,348 A | 12/1999 | Banas et al. |
| 6,009,877 A | 1/2000 | Edwards |
| 6,012,457 A | 1/2000 | Lesh |
| 6,024,740 A | 2/2000 | Lesh et al. |
| 6,032,077 A | 2/2000 | Pomeranz |
| 6,036,687 A | 3/2000 | Laufer et al. |
| 6,042,578 A | 3/2000 | Dinh et al. |
| 6,048,329 A | 4/2000 | Thompson et al. |
| 6,064,902 A | 5/2000 | Haissaguerre et al. |
| 6,066,134 A | 5/2000 | Eggers et al. |
| 6,071,729 A | 6/2000 | Jeffries et al. |
| 6,074,339 A | 6/2000 | Gambale et al. |
| 6,074,361 A | 6/2000 | Jacobs |
| 6,074,378 A | 6/2000 | Mouri et al. |
| 6,076,012 A | 6/2000 | Swanson et al. |
| 6,078,840 A | 6/2000 | Stokes |
| 6,078,841 A | 6/2000 | Kuzma |
| 6,090,104 A | 7/2000 | Webster, Jr. |
| 6,091,995 A | 7/2000 | Ingle et al. |
| 6,094,596 A | 7/2000 | Morgan |
| 6,096,036 A | 8/2000 | Bowe et al. |
| 6,099,524 A | 8/2000 | Lipson et al. |
| 6,106,522 A | 8/2000 | Fleischman et al. |
| 6,117,101 A | 9/2000 | Diederich et al. |
| 6,125,302 A | 9/2000 | Kuzma |
| 6,129,750 A | 10/2000 | Tockman et al. |
| 6,132,456 A | 10/2000 | Sommer et al. |
| 6,135,999 A | 10/2000 | Fanton et al. |
| 6,146,381 A | 11/2000 | Bowe et al. |
| 6,149,620 A | 11/2000 | Baker et al. |
| 6,152,912 A | 11/2000 | Jansen et al. |
| 6,156,046 A | 12/2000 | Passafaro et al. |
| 6,161,048 A | 12/2000 | Sluijter et al. |
| 6,161,049 A | 12/2000 | Rudie et al. |
| 6,164,283 A | 12/2000 | Lesh |
| 6,190,356 B1 | 2/2001 | Bersin |
| 6,214,002 B1 | 4/2001 | Fleischman et al. |
| 6,219,577 B1 | 4/2001 | Brown, III et al. |
| 6,223,070 B1 | 4/2001 | Chait |
| 6,224,592 B1 | 5/2001 | Eggers et al. |
| 6,228,109 B1 | 5/2001 | Tu et al. |
| 6,246,912 B1 | 6/2001 | Sluijter et al. |
| 6,270,496 B1 | 8/2001 | Bowe et al. |
| 6,273,886 B1 | 8/2001 | Edwards et al. |
| 6,280,441 B1 | 8/2001 | Ryan |
| 6,283,951 B1 | 9/2001 | Flaherty et al. |
| 6,292,695 B1 | 9/2001 | Webster, Jr. et al. |
| 6,308,090 B1 | 10/2001 | Tu et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,325,797 B1 | 12/2001 | Stewart et al. |
| 6,364,904 B1 | 4/2002 | Smith |
| 6,385,472 B1 | 5/2002 | Hall et al. |
| 6,405,732 B1 | 6/2002 | Edwards et al. |
| 6,409,742 B1 | 6/2002 | Fulton, III et al. |
| 6,413,255 B1 | 7/2002 | Stern |
| 6,430,426 B2 | 8/2002 | Avitall |
| 6,436,056 B1 | 8/2002 | Wang et al. |
| 6,442,415 B1 | 8/2002 | Bis et al. |
| 6,451,045 B1 | 9/2002 | Walker et al. |
| 6,454,775 B1 | 9/2002 | Demarais et al. |
| 6,480,747 B2 | 11/2002 | Schmidt |
| 6,488,679 B1 | 12/2002 | Swanson et al. |
| 6,496,737 B2 | 12/2002 | Rudie et al. |
| 6,500,174 B1 | 12/2002 | Maguire et al. |
| 6,506,189 B1 | 1/2003 | Rittman, III et al. |
| 6,508,804 B2 | 1/2003 | Sarge et al. |
| 6,511,492 B1 | 1/2003 | Rosenbluth et al. |
| 6,514,226 B1 | 2/2003 | Levin et al. |
| 6,514,249 B1 | 2/2003 | Maguire et al. |
| 6,522,926 B1 | 2/2003 | Kieval et al. |
| 6,527,739 B1 | 3/2003 | Bigus et al. |
| 6,529,756 B1 | 3/2003 | Phan et al. |
| 6,530,935 B2 | 3/2003 | Wensel et al. |
| 6,540,734 B1 | 4/2003 | Chiu et al. |
| 6,542,781 B1 | 4/2003 | Koblish et al. |
| 6,546,272 B1 | 4/2003 | MacKinnon et al. |
| 6,546,280 B2 | 4/2003 | Osborne |
| 6,562,031 B2 | 5/2003 | Chandrasekaran et al. |
| 6,562,034 B2 | 5/2003 | Edwards et al. |
| 6,564,096 B2 | 5/2003 | Mest |
| 6,565,562 B1 | 5/2003 | Shah et al. |
| 6,572,612 B2 | 6/2003 | Stewart et al. |
| 6,592,581 B2 | 7/2003 | Bowe |
| 6,602,242 B1 | 8/2003 | Fung et al. |
| 6,605,061 B2 | 8/2003 | VanTassel et al. |
| 6,607,520 B2 | 8/2003 | Keane |
| 6,610,046 B1 | 8/2003 | Usami et al. |
| 6,610,083 B2 | 8/2003 | Keller et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,623,515 B2 | 9/2003 | Mulier et al. |
| 6,628,976 B1 | 9/2003 | Fuimaono et al. |
| 6,635,054 B2 | 10/2003 | Fjield et al. |
| 6,652,517 B1 | 11/2003 | Hall et al. |
| 6,685,648 B2 | 2/2004 | Flaherty et al. |
| 6,692,490 B1 | 2/2004 | Edwards |
| 6,702,811 B2 | 3/2004 | Stewart et al. |
| 6,711,444 B2 | 3/2004 | Koblish |
| 6,736,835 B2 | 5/2004 | Pellegrino et al. |
| 6,745,080 B2 | 6/2004 | Koblish |
| 6,746,474 B2 | 6/2004 | Saadat |
| 6,752,805 B2 | 6/2004 | Maguire et al. |
| 6,758,830 B1 | 7/2004 | Schaer et al. |
| 6,773,433 B2 | 8/2004 | Stewart et al. |
| 6,780,183 B2 | 8/2004 | Jimenez, Jr. et al. |
| 6,802,840 B2 | 10/2004 | Chin et al. |
| 6,802,857 B1 | 10/2004 | Walsh et al. |
| 6,814,733 B2 | 11/2004 | Schwartz et al. |
| 6,817,999 B2 | 11/2004 | Berube et al. |
| 6,845,267 B2 | 1/2005 | Harrison et al. |
| 6,847,848 B2 | 1/2005 | Sterzer et al. |
| 6,850,801 B2 | 2/2005 | Kieval et al. |
| 6,869,431 B2 | 3/2005 | Maguire et al. |
| 6,882,886 B1 | 4/2005 | Witte et al. |
| 6,885,888 B2 | 4/2005 | Rezai |
| 6,890,329 B2 | 5/2005 | Carroll et al. |
| 6,893,436 B2 | 5/2005 | Woodard et al. |
| 6,893,438 B2 | 5/2005 | Hall et al. |
| 6,899,711 B2 | 5/2005 | Stewart et al. |
| 6,905,510 B2 | 6/2005 | Saab |
| 6,909,920 B2 | 6/2005 | Lokhoff et al. |
| 6,923,808 B2 | 8/2005 | Taimisto |
| 6,939,346 B2 | 9/2005 | Kannenberg et al. |
| 6,941,953 B2 | 9/2005 | Feld et al. |
| 6,949,097 B2 | 9/2005 | Stewart et al. |
| 6,952,615 B2 | 10/2005 | Satake |
| 6,960,206 B2 | 11/2005 | Keane |
| 6,960,207 B2 | 11/2005 | Vanney et al. |
| 6,972,016 B2 | 12/2005 | Hill, III et al. |
| 7,013,169 B2 | 3/2006 | Bowe |

(56) References Cited

U.S. PATENT DOCUMENTS

| | | |
|---|---|---|
| 7,013,170 B2 | 3/2006 | Bowe |
| 7,058,456 B2 | 6/2006 | Pierce |
| 7,063,719 B2 | 6/2006 | Jansen et al. |
| 7,081,115 B2 | 7/2006 | Taimisto |
| 7,104,988 B2 | 9/2006 | Altman et al. |
| 7,110,828 B2 | 9/2006 | Kolberg et al. |
| 7,115,134 B2 | 10/2006 | Chambers |
| 7,149,574 B2 | 12/2006 | Yun et al. |
| 7,155,271 B2 | 12/2006 | Halperin et al. |
| 7,158,832 B2 | 1/2007 | Kieval et al. |
| 7,162,303 B2 | 1/2007 | Levin et al. |
| 7,184,811 B2 | 2/2007 | Phan et al. |
| 7,201,738 B1 | 4/2007 | Bengmark |
| 7,211,082 B2 | 5/2007 | Hall et al. |
| 7,221,979 B2 | 5/2007 | Zhou et al. |
| 7,232,458 B2 | 6/2007 | Saadat |
| 7,254,451 B2 | 8/2007 | Seifert et al. |
| 7,264,619 B2 | 9/2007 | Venturelli |
| 7,282,213 B2 | 10/2007 | Schroeder et al. |
| 7,285,119 B2 | 10/2007 | Stewart et al. |
| 7,291,146 B2 | 11/2007 | Steinke et al. |
| 7,311,705 B2 | 12/2007 | Sra |
| 7,381,200 B2 | 6/2008 | Katoh et al. |
| 7,390,894 B2 | 6/2008 | Weinshilboum et al. |
| 7,404,824 B1 | 7/2008 | Webler et al. |
| 7,435,248 B2 | 10/2008 | Taimisto et al. |
| 7,517,349 B2 | 4/2009 | Truckai et al. |
| 7,526,343 B2 | 4/2009 | Peterson et al. |
| 7,542,808 B1 | 6/2009 | Peterson et al. |
| 7,597,704 B2 | 10/2009 | Frazier et al. |
| 7,617,005 B2 | 11/2009 | Demarais et al. |
| 7,620,451 B2 | 11/2009 | Demarais et al. |
| 7,637,903 B2 | 12/2009 | Lentz et al. |
| 7,646,544 B2 | 1/2010 | Batchko et al. |
| 7,647,115 B2 | 1/2010 | Levin et al. |
| 7,647,124 B2 | 1/2010 | Williams |
| 7,653,438 B2 | 1/2010 | Deem et al. |
| 7,670,335 B2 | 3/2010 | Keidar |
| 7,682,319 B2 | 3/2010 | Martin et al. |
| 7,717,853 B2 | 5/2010 | Nita |
| 7,717,948 B2 | 5/2010 | Demarais et al. |
| 7,727,178 B2 | 6/2010 | Wilson et al. |
| 7,729,782 B2 | 6/2010 | Williams et al. |
| 7,747,334 B2 | 6/2010 | Bly et al. |
| 7,771,421 B2 | 8/2010 | Stewart et al. |
| 7,778,703 B2 | 8/2010 | Gross et al. |
| 7,789,877 B2 | 9/2010 | Vanney |
| 7,806,871 B2 | 10/2010 | Li et al. |
| 7,850,685 B2 | 12/2010 | Kunis et al. |
| 7,863,897 B2 | 1/2011 | Slocum, Jr. et al. |
| 7,867,219 B2 | 1/2011 | Chambers |
| 7,881,807 B2 | 2/2011 | Schaer |
| 7,890,188 B2 | 2/2011 | Zhang et al. |
| 7,927,370 B2 | 4/2011 | Webler et al. |
| 7,942,928 B2 | 5/2011 | Webler et al. |
| 7,959,630 B2 | 6/2011 | Taimisto et al. |
| 8,019,435 B2 | 9/2011 | Hastings et al. |
| 8,062,284 B2 | 11/2011 | Booth |
| 8,100,859 B2 | 1/2012 | Patterson et al. |
| 8,123,739 B2 | 2/2012 | McQueen et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,428 B2 | 6/2012 | Truckai et al. |
| 8,257,351 B2 | 9/2012 | Stewart et al. |
| 8,308,722 B2 | 11/2012 | Ormsby et al. |
| 8,337,492 B2 | 12/2012 | Kunis et al. |
| 8,380,275 B2 | 2/2013 | Kim et al. |
| 8,398,629 B2 | 3/2013 | Thistle |
| 8,480,663 B2 | 7/2013 | Ingle et al. |
| 8,571,665 B2 | 10/2013 | Moffitt |
| 9,014,821 B2 | 4/2015 | Wang |
| 9,055,956 B2 | 6/2015 | McRae et al. |
| 2001/0005785 A1 | 6/2001 | Sachse |
| 2001/0007070 A1 | 7/2001 | Stewart et al. |
| 2001/0020174 A1 | 9/2001 | Koblish |
| 2001/0023365 A1 | 9/2001 | Medhkour et al. |
| 2001/0031971 A1 | 10/2001 | Dretler et al. |
| 2002/0004631 A1 | 1/2002 | Jenkins et al. |
| 2002/0004644 A1 | 1/2002 | Koblish |
| 2002/0042610 A1 | 4/2002 | Sliwa et al. |
| 2002/0062124 A1 | 5/2002 | Keane |
| 2002/0087208 A1 | 7/2002 | Koblish et al. |
| 2002/0107515 A1 | 8/2002 | Edwards et al. |
| 2002/0128639 A1 | 9/2002 | Pless et al. |
| 2002/0139379 A1 | 10/2002 | Edwards et al. |
| 2002/0165532 A1 | 11/2002 | Hill et al. |
| 2002/0169444 A1 | 11/2002 | Mest et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060857 A1 | 3/2003 | Perrson et al. |
| 2003/0060858 A1 | 3/2003 | Kieval et al. |
| 2003/0065317 A1 | 4/2003 | Rudie et al. |
| 2003/0074039 A1 | 4/2003 | Puskas |
| 2003/0088244 A1 | 5/2003 | Swanson et al. |
| 2003/0125790 A1 | 7/2003 | Fastovsky et al. |
| 2003/0153967 A1 | 8/2003 | Koblish et al. |
| 2003/0158584 A1 | 8/2003 | Cates et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0204187 A1 | 10/2003 | Hintringer |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0024371 A1 | 2/2004 | Plicchi et al. |
| 2004/0030375 A1 | 2/2004 | Pierce |
| 2004/0049181 A1* | 3/2004 | Stewart ............ A61B 18/1492 606/41 |
| 2004/0082978 A1 | 4/2004 | Harrison et al. |
| 2004/0122421 A1 | 6/2004 | Wood |
| 2004/0167509 A1 | 8/2004 | Taimisto |
| 2004/0215186 A1 | 10/2004 | Cornelius et al. |
| 2004/0260278 A1 | 12/2004 | Anderson et al. |
| 2005/0010095 A1 | 1/2005 | Stewart et al. |
| 2005/0033274 A1 | 2/2005 | Pless et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2005/0251125 A1 | 11/2005 | Pless et al. |
| 2006/0004352 A1 | 1/2006 | Vaska et al. |
| 2006/0074403 A1 | 4/2006 | Rafiee |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0135870 A1 | 6/2006 | Webler |
| 2006/0135953 A1 | 6/2006 | Kania et al. |
| 2006/0174129 A1 | 8/2006 | Brignone et al. |
| 2006/0200119 A1 | 9/2006 | Vaska et al. |
| 2006/0206150 A1 | 9/2006 | Demarais et al. |
| 2006/0212076 A1 | 9/2006 | Demarais et al. |
| 2006/0241366 A1 | 10/2006 | Falwell et al. |
| 2006/0247618 A1 | 11/2006 | Kaplan et al. |
| 2006/0247619 A1 | 11/2006 | Kaplan et al. |
| 2006/0271111 A1 | 11/2006 | Demarais et al. |
| 2007/0043409 A1 | 2/2007 | Brian et al. |
| 2007/0083194 A1 | 4/2007 | Kunis et al. |
| 2007/0129720 A1 | 6/2007 | Demarais et al. |
| 2007/0225781 A1 | 9/2007 | Saadat et al. |
| 2007/0265687 A1 | 11/2007 | Deem et al. |
| 2008/0021408 A1 | 1/2008 | Jacobsen et al. |
| 2008/0045921 A1 | 2/2008 | Anderson et al. |
| 2008/0064957 A1 | 3/2008 | Spence |
| 2008/0097398 A1 | 4/2008 | Mitelberg et al. |
| 2008/0108975 A1 | 5/2008 | Appling et al. |
| 2008/0109011 A1 | 5/2008 | Thenuwara et al. |
| 2008/0161774 A1 | 7/2008 | Hastings et al. |
| 2008/0172104 A1 | 7/2008 | Kieval et al. |

(56) References Cited

U.S. PATENT DOCUMENTS

| | | |
|---|---|---|
| 2008/0255539 A1 | 10/2008 | Booth |
| 2008/0255642 A1 | 10/2008 | Zarins et al. |
| 2008/0288039 A1 | 11/2008 | Reddy |
| 2008/0300587 A1 | 12/2008 | Anderson |
| 2008/0319513 A1 | 12/2008 | Pu et al. |
| 2009/0018534 A1 | 1/2009 | Taimisto et al. |
| 2009/0036948 A1 | 2/2009 | Levin et al. |
| 2009/0287202 A1 | 11/2009 | Ingle et al. |
| 2009/0306650 A1 | 12/2009 | Govari et al. |
| 2009/0312606 A1 | 12/2009 | Dayton et al. |
| 2010/0030112 A1 | 2/2010 | Anderson et al. |
| 2010/0049192 A1 | 2/2010 | Holtz et al. |
| 2010/0137860 A1 | 6/2010 | Demarais et al. |
| 2010/0137952 A1 | 6/2010 | Demarais et al. |
| 2010/0168777 A1 | 7/2010 | Stangenes et al. |
| 2010/0170519 A1 | 7/2010 | Romo et al. |
| 2010/0174282 A1 | 7/2010 | Demaris et al. |
| 2010/0179512 A1 | 7/2010 | Chong et al. |
| 2010/0191112 A1 | 7/2010 | Demarais et al. |
| 2010/0204692 A1 | 8/2010 | Stewart et al. |
| 2010/0222851 A1 | 9/2010 | Deem et al. |
| 2010/0222854 A1 | 9/2010 | Demarais et al. |
| 2010/0261990 A1 | 10/2010 | Gillis et al. |
| 2011/0021976 A1 | 1/2011 | Li et al. |
| 2011/0144639 A1 | 6/2011 | Govari |
| 2011/0160719 A1 | 6/2011 | Govari et al. |
| 2011/0196298 A1 | 8/2011 | Anderson et al. |
| 2011/0264086 A1 | 10/2011 | Ingle |
| 2011/0276024 A1 | 11/2011 | Randolph et al. |
| 2011/0306851 A1 | 12/2011 | Wang |
| 2011/0319908 A1 | 12/2011 | Thenuwara et al. |
| 2012/0010607 A1 | 1/2012 | Malecki et al. |
| 2012/0029509 A1 | 2/2012 | Smith |
| 2012/0029510 A1 | 2/2012 | Haverkost |
| 2012/0029513 A1 | 2/2012 | Smith et al. |
| 2012/0035615 A1 | 2/2012 | Koester et al. |
| 2012/0078076 A1 | 3/2012 | Stewart et al. |
| 2012/0101553 A1 | 4/2012 | Reddy |
| 2012/0116382 A1 | 5/2012 | Ku et al. |
| 2012/0116383 A1 | 5/2012 | Mauch et al. |
| 2012/0116438 A1 | 5/2012 | Salahieh et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130368 A1 | 5/2012 | Jenson |
| 2012/0143293 A1 | 6/2012 | Mauch et al. |
| 2012/0172837 A1 | 7/2012 | Demarais et al. |
| 2012/0191083 A1 | 7/2012 | Moll et al. |
| 2012/0197246 A1 | 8/2012 | Mauch |
| 2012/0220879 A1 | 8/2012 | Fandrey et al. |
| 2012/0277842 A1 | 11/2012 | Kunis |
| 2012/0290053 A1 | 11/2012 | Zhang et al. |
| 2012/0310065 A1 | 12/2012 | Falwell et al. |
| 2012/0310239 A1 | 12/2012 | Stewart et al. |
| 2012/0323233 A1 | 12/2012 | Maguire et al. |
| 2013/0053876 A1 | 2/2013 | Ogle |
| 2013/0066316 A1 | 3/2013 | Steinke et al. |
| 2013/0085360 A1 | 4/2013 | Grunewald |
| 2013/0090637 A1 | 4/2013 | Sliwa |
| 2013/0165920 A1 | 6/2013 | Weber et al. |
| 2013/0165921 A1* | 6/2013 | Sutermeister ...... A61B 18/1492 606/41 |
| 2013/0172872 A1 | 7/2013 | Subramaniam et al. |
| 2013/0172879 A1 | 7/2013 | Sutermeister et al. |
| 2013/0172880 A1* | 7/2013 | Willard ............. A61B 18/1492 606/41 |
| 2013/0184703 A1 | 7/2013 | Shireman et al. |
| 2013/0184773 A1 | 7/2013 | Libbus |
| 2013/0253628 A1 | 9/2013 | Smith et al. |
| 2013/0274614 A1 | 10/2013 | Shimada |
| 2013/0274730 A1 | 10/2013 | Anderson |
| 2013/0274731 A1 | 10/2013 | Anderson |
| 2013/0274737 A1 | 10/2013 | Wang |
| 2013/0282000 A1 | 10/2013 | Parsonage |
| 2013/0282084 A1 | 10/2013 | Mathur et al. |
| 2013/0289686 A1 | 10/2013 | Masson |
| 2013/0304047 A1 | 11/2013 | Grunewald |
| 2013/0304052 A1 | 11/2013 | Rizq |
| 2013/0304061 A1 | 11/2013 | Chang et al. |
| 2013/0304062 A1* | 11/2013 | Chan ................. A61B 18/1492 606/41 |
| 2014/0058376 A1 | 2/2014 | Horn |
| 2014/0213873 A1 | 7/2014 | Wang |
| 2014/0214018 A1 | 7/2014 | Behar et al. |
| 2014/0221805 A1 | 8/2014 | Wang |
| 2014/0243821 A1 | 8/2014 | Salahieh et al. |
| 2014/0249524 A1 | 9/2014 | Kocur |
| 2014/0257280 A1 | 9/2014 | Hanson et al. |
| 2014/0257281 A1 | 9/2014 | Squire et al. |
| 2014/0276747 A1 | 9/2014 | Abunassar et al. |
| 2014/0276787 A1 | 9/2014 | Wang et al. |
| 2014/0276789 A1 | 9/2014 | Dandler et al. |
| 2014/0303617 A1 | 10/2014 | Shimada |
| 2014/0350553 A1 | 11/2014 | Okuyama |
| 2015/0057655 A1 | 2/2015 | Osypka |
| 2015/0112329 A1 | 4/2015 | Ng |
| 2015/0126992 A1 | 5/2015 | Mogul |

FOREIGN PATENT DOCUMENTS

| | | |
|---|---|---|
| AU | 2011239320 | 5/2012 |
| CN | 101309651 | 11/2008 |
| CN | 201469401 | 5/2010 |
| CN | 102198015 | 9/2011 |
| CN | 102274075 | 12/2011 |
| CN | 102488552 | 6/2012 |
| CN | 202386778 | 8/2012 |
| CN | 202426649 | 9/2012 |
| CN | 202537649 | 11/2012 |
| CN | 202538132 | 11/2012 |
| CN | 102885648 | 1/2013 |
| CN | 102885649 | 1/2013 |
| CN | 102908188 | 2/2013 |
| CN | 102908189 | 2/2013 |
| CN | 202761434 | 3/2013 |
| CN | 103027745 | 4/2013 |
| CN | 103027746 | 4/2013 |
| CN | 103027747 | 4/2013 |
| CN | 202843784 | 4/2013 |
| DE | 29909082 | 7/1999 |
| DE | 10252325 | 5/2004 |
| DE | 10257146 | 6/2004 |
| EP | 0132344 | 1/1986 |
| EP | 0510624 | 10/1992 |
| EP | 510624 | 7/1995 |
| EP | 732080 | 9/1996 |
| EP | 0779079 | 6/1997 |
| EP | 0821602 | 2/1998 |
| EP | 865256 | 9/1998 |
| EP | 868160 | 10/1998 |
| EP | 0868923 | 10/1998 |
| EP | 0728495 | 4/1999 |
| EP | 0916360 | 5/1999 |
| EP | 1233716 | 8/2002 |
| EP | 1297795 | 4/2003 |
| EP | 963191 | 8/2003 |
| EP | 1332724 | 8/2003 |
| EP | 757575 | 9/2003 |
| EP | 873760 | 1/2004 |
| EP | 1383567 | 1/2004 |
| EP | 779079 | 3/2004 |
| EP | 0778043 | 11/2005 |
| EP | 1042990 | 10/2006 |
| EP | 1733689 | 12/2006 |
| EP | 1802370 | 7/2007 |
| EP | 1009303 | 6/2009 |
| EP | 2208474 | 7/2010 |
| EP | 2263588 | 12/2010 |
| EP | 2329859 | 6/2011 |
| EP | 2519173 | 11/2012 |
| EP | 2558016 | 2/2013 |
| EP | 2570154 | 3/2013 |
| EP | 2598069 | 6/2013 |
| EP | 2664295 | 11/2013 |

(56) References Cited

FOREIGN PATENT DOCUMENTS

| | | |
|---|---|---|
| EP | 2694158 | 2/2014 |
| EP | 2759275 | 7/2014 |
| EP | 2760532 | 8/2014 |
| EP | 2804554 | 11/2014 |
| JP | 355137141 | 10/1980 |
| JP | 2008515544 | 5/2008 |
| JP | 2009500052 | 1/2009 |
| WO | WO-9115254 | 10/1991 |
| WO | WO-9220291 | 11/1992 |
| WO | WO-9407446 | 4/1994 |
| WO | WO-9421168 | 9/1994 |
| WO | WO-9513111 | 5/1995 |
| WO | WO-9520416 | 8/1995 |
| WO | WO-9525472 | 9/1995 |
| WO | WO 9531142 | 11/1995 |
| WO | WO-9600036 | 1/1996 |
| WO | WO-9632980 | 10/1996 |
| WO | WO-9638196 | 12/1996 |
| WO | WO9717892 | 5/1997 |
| WO | WO-9736548 | 10/1997 |
| WO | WO-9802201 | 1/1998 |
| WO | WO-9818393 | 5/1998 |
| WO | WO-9833469 | 8/1998 |
| WO | WO-9843530 | 10/1998 |
| WO | WO 9900060 | 1/1999 |
| WO | WO-9923958 | 5/1999 |
| WO | WO-9952421 | 10/1999 |
| WO | WO-9956801 | 11/1999 |
| WO | WO-9962413 | 12/1999 |
| WO | WO-0001313 | 1/2000 |
| WO | WO-0056237 | 9/2000 |
| WO | WO-0067832 | 11/2000 |
| WO | WO-0122897 | 4/2001 |
| WO | WO-0137723 | 5/2001 |
| WO | WO-0137746 | 5/2001 |
| WO | WO-0170114 | 9/2001 |
| WO | WO-0174255 | 10/2001 |
| WO | WO-0180758 | 11/2001 |
| WO | WO-0245608 | 6/2002 |
| WO | WO-02083017 | 10/2002 |
| WO | WO-02087453 | 11/2002 |
| WO | WO-02089687 | 11/2002 |
| WO | WO-02089908 | 11/2002 |
| WO | WO-03022167 | 3/2003 |
| WO | WO-03077781 | 9/2003 |
| WO | WO-03082080 | 10/2003 |
| WO | WO-2004100813 | 11/2004 |
| WO | WO-2005030072 | 4/2005 |
| WO | WO-2005041748 | 5/2005 |
| WO | WO-2005051216 | 6/2005 |
| WO | WO-2005070491 | 8/2005 |
| WO | WO-2005110528 | 11/2005 |
| WO | WO-2006020920 | 2/2006 |
| WO | WO-2006041881 | 4/2006 |
| WO | WO-2006065949 | 6/2006 |
| WO | WO-2006092000 | 9/2006 |
| WO | WO 2006105121 | 10/2006 |
| WO | WO-2007001981 | 1/2007 |
| WO | WO-2007008954 | 1/2007 |
| WO | WO 2007078997 | 7/2007 |
| WO | WO-2007128064 | 11/2007 |
| WO | WO2008049084 | 4/2008 |
| WO | WO-2008101244 | 8/2008 |
| WO | WO-2009121017 | 1/2009 |
| WO | WO-2009082635 | 7/2009 |
| WO | WO-2010048676 | 5/2010 |
| WO | WO-2010091701 | 8/2010 |
| WO | WO-2010120835 | 10/2010 |
| WO | WO-2011015218 | 2/2011 |
| WO | WO-2011019838 | 2/2011 |
| WO | WO-2011/060200 | 5/2011 |
| WO | WO-2011055143 | 5/2011 |
| WO | WO-2011082279 | 7/2011 |
| WO | WO-2011130534 | 10/2011 |
| WO | WO-2012061159 | 5/2012 |
| WO | WO-2012061161 | 5/2012 |
| WO | WO-2012061164 | 5/2012 |
| WO | WO-2012075156 | 6/2012 |
| WO | WO-2012130337 | 10/2012 |
| WO | WO-2012131107 | 10/2012 |
| WO | WO-2012154219 | 11/2012 |
| WO | WO-2012154796 | 11/2012 |
| WO | WO-2013016203 | 1/2013 |
| WO | WO-2013028993 | 2/2013 |
| WO | WO-2013030807 | 3/2013 |
| WO | WO-2013040201 | 3/2013 |
| WO | WO-2013049601 | 4/2013 |
| WO | WO-2013101452 | 7/2013 |
| WO | WO-2013106054 | 7/2013 |
| WO | WO 2013109318 | 7/2013 |
| WO | WO 2013158676 | 10/2013 |
| WO | WO 2013158678 | 10/2013 |
| WO | WO 2013165920 | 11/2013 |
| WO | WO-2013169340 | 11/2013 |
| WO | WO 2013154776 | 12/2013 |
| WO | WO-2014036160 | 3/2014 |
| WO | WO-2014036163 | 3/2014 |
| WO | WO-2014056460 | 4/2014 |
| WO | WO-2014163987 | 10/2014 |
| WO | WO-2014163990 | 10/2014 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

(56) References Cited

OTHER PUBLICATIONS

Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
International Search Report and Written Opinion for International Application No. PCT/US2013/030207, mailed Sep. 23, 2013, 19 pages.
European Search Report for European Application No. 13159256, Date Mailed: Oct. 17, 2013, 6 pages.
International Search Report, PCT/US02/07661, Aug. 13, 2002, 5 Pages.
International Search Report, PCT/US03/031339, Feb. 18, 2004, 3 Pages.
International Search Report, PCT/US01/044977, Jun. 7, 2002, 6 Pages.
Claudine Jaboro, "An in vivo study of the biocompatibility of classic and novel device materials on the central nervous system", (Jan. 1, 2007), ETD Collection for Wayne State University. Paper AA13310737, 2 pages. <http://digitalcommons.wayne.edu/dissertations/AA13310737>.
European Search Report dated Jan. 30, 2013; European Application No. 12180426.4; Applicant: Medtronic Ardian Luxembourg S.a.r.l.; 6 pages.
European Search Report dated Feb. 28, 2013; European Application No. 12180427.2; Applicant: Medtronic Ardian Luxembourg S.a.r.l.; 4 pages.
European Search Report dated Jan. 30, 2013; Application No. 12180428.0; Applicant: Medtronic Ardian Luxembourg S.a.r.l.; 6 pages.
European Search Report dated Jan. 30, 2013; Application No. 12180430.6; Applicant: Medtronic Ardian Luxembourg S.a.r.l.; 6 pages.
European Search Report dated Jan. 30, 2013; Application No. 12180431.4; Applicant: Medtronic Ardian Luxembourg S.a.r.l.; 6 pages.
European Search Report dated Feb. 22, 2013; Application No. 12180432.2; Applicant: Medtronic Ardian Luxembourg S.a.r.l.; 6 pages.
International Search Report and Written Opinion dated Jan. 23, 2012, International Application No. PCT/US2011/057761, 13 pages.
International Search Report and Written Opinion dated Jan. 20, 2012, International Application No. PCT/US2011/057756, 10 pages.
International Search Report and Written Opinion dated Feb. 16, 2012, International Application No. PCT/US2011/057754, 13 pages.
Lahiri D. et al. "Boron nitride nanotube reinforced polylactide-polycaprolactone copolymer composite: Mechanical properties and cytocompatibility with osteoblasts and macrophages in vitro." Acta Biomater (2010), doi: 10.1016/j.actbio.2010.02.44, 10 pages.
Hanker et al., "Biomedical Materials and Devices," Materials Research Society Symposium Proceedings, vol. 110, Dec. 4, 1987, Boston Massachusetts, USA, 8 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operators Manual of Boston Scientific's EPT-1000 XP Cardiac Ablation Controller & Accessories, Version of Apr. 2003, (6 pages).
Excerpt of Operators Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 60/852,787, filed Oct. 18, 2006, 105 pages.

(56) References Cited

OTHER PUBLICATIONS

Pieper et al., "Design and Implementation of a New Computerized System for Intraoperative Cardiac Mapping." Journal of Applied Physiology, 1991, vol. 71, No. 4, pp. 1529-1539.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al. "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-54.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.

(56) References Cited

OTHER PUBLICATIONS

Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011)44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding A Future For Renal Denervation With Better Controlled Trials," Pharma & Medtech Business Intelligence, Article # 01141006003, Oct. 6, 2014, 4 pages.
Papdemetriou, Vasilios, "Renal Denervation and Symplicity HTN-3: "Dubium Sapientiae Initium" (Doubt Is the Beginning of Wisdom)", Circulation Research, 2014; 115: 211-214.
Papdemetriou, Vasilios, "Renal Nerve Ablation for Resistant Hypertension: How Did We Get Here, Present Status, and Future Directions." Circulation. 2014; 129: 1440-1450.
Papdemetriou, Vasilios, "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.

* cited by examiner

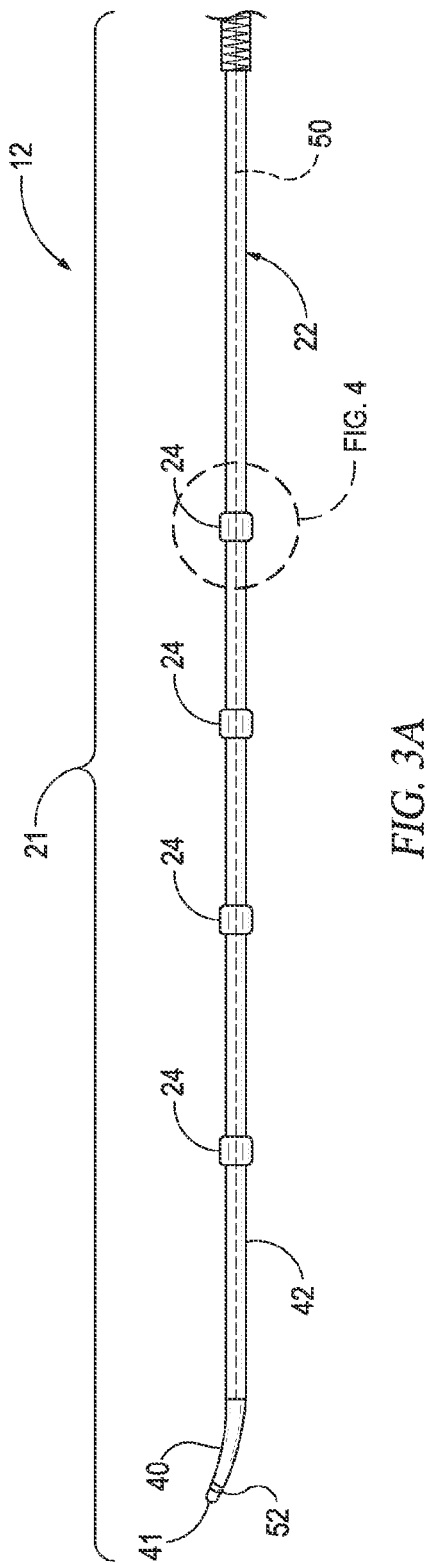

MULTI-ELECTRODE CATHETER ASSEMBLIES FOR RENAL NEUROMODULATION AND ASSOCIATED SYSTEMS AND METHODS

CROSS REFERENCE TO RELATED APPLICATION(S)

The present application is a continuation of U.S. patent application Ser. No. 14/511,078 filed Oct. 9, 2014, now U.S. Pat. No. 9,138,292, which is a continuation of U.S. patent application Ser. No. 13/793,647 filed Mar. 11, 2013, now U.S. Pat. No. 8,888,773, which claims the benefit of and priority to U.S. Provisional Patent Application No. 61/646,218, filed May 11, 2012, all of which are incorporated herein by reference in their entirety.

ADDITIONAL APPLICATIONS INCORPORATED BY REFERENCE

The following applications are also incorporated herein by reference in their entireties:

U.S. patent application Ser. No. 13/281,360, filed Oct. 25, 2011, now abandoned;

U.S. patent application Ser. No. 13/281,361, filed Oct. 25, 2011, now U.S. Pat. No. 8,998,894; and U.S. patent application Ser. No. 13/281,395, filed Oct. 25, 2011, now U.S. Pat. No. 8,956,352.

As such, components and features of embodiments disclosed in these applications may be combined with various components and features disclosed in the present application.

TECHNICAL FIELD

The present technology relates generally to renal neuromodulation and associated systems and methods. In particular, several embodiments are directed to multi-electrode radio frequency (RF) ablation catheter assemblies for intravascular renal neuromodulation and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys of plasma is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via RF ablation) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIG. 3A is a side view of a distal portion of a catheter having a therapeutic assembly or treatment section in a delivery state (e.g., low-profile or collapsed configuration) outside a patient in accordance with an embodiment of the present technology.

DETAILED DESCRIPTION

Figure 1:
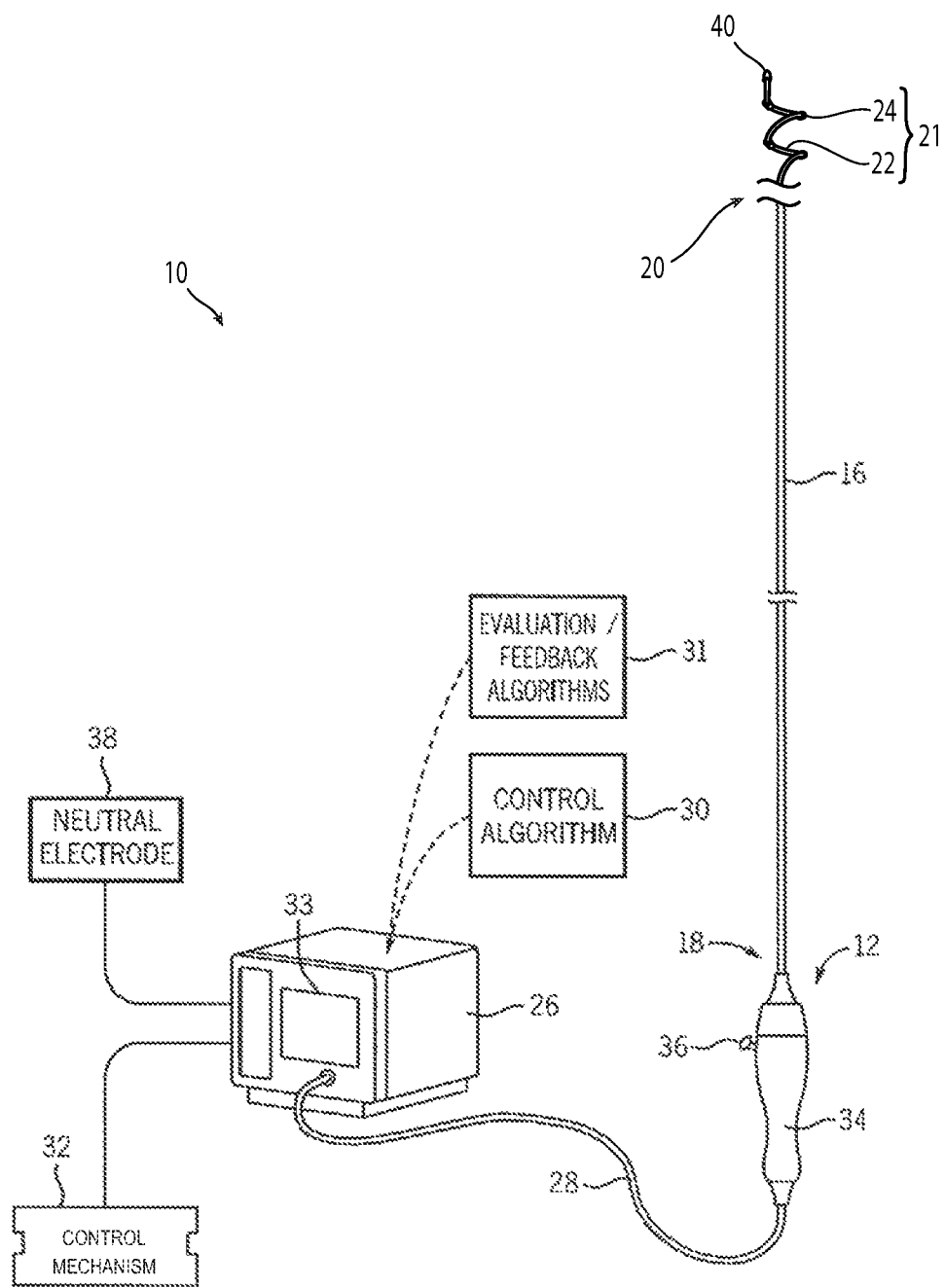
FIG. 1 is a partially schematic diagram of a neuromodulation system configured in accordance with an embodiment of the present technology.

The present technology is directed to apparatuses, systems, and methods for achieving electrically- and/or thermally-induced renal neuromodulation (i.e., rendering neural fibers that innervate the kidney inert or inactive or otherwise completely or partially reduced in function) by percutaneous transluminal intravascular access. In particular, embodiments of the present technology relate to catheters and catheter assemblies having multi-electrode arrays and being movable between a delivery or low-profile state (e.g., a generally straight shape) and a deployed state (e.g., a radially expanded, generally helical shape). The electrodes or energy delivery elements comprising the multi-electrode array are configured to deliver energy (e.g., electrical energy, RF energy, pulsed electrical energy, thermal energy) to a renal artery after being advanced thereto via a catheter along a percutaneous transluminal path (e.g., a femoral artery puncture, an iliac artery and the aorta, a radial artery, or another suitable intravascular path). The catheter or catheter assembly carrying the multi-electrode array is sized and shaped so that the electrodes or energy delivery elements contact an interior wall of the renal artery when the catheter is in the deployed (e.g., helical) state within the renal artery. In addition, the helical shape of the deployed portion of the catheter carrying the array allows blood to flow through the helix, which is expected to help prevent occlusion of the renal artery during activation of the energy delivery element. Further, blood flow in and around the array may cool the associated energy delivery elements and/or the surrounding tissue. In some embodiments, cooling the energy delivery elements allows for the delivery of higher power levels at lower temperatures than may be reached without cooling. This feature is expected to help create deeper and/or larger lesions during therapy, reduce intimal surface temperature, and/or allow longer activation times with reduced risk of overheating during treatment.

Specific details of several embodiments of the technology are described below with reference to FIGS. 1-5. Although many of the embodiments are described below with respect to devices, systems, and methods for intravascular modulation of renal nerves using multi-electrode arrays, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-5.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves.

Various techniques can be used to partially or completely incapacitate neural pathways, such as those innervating the kidney. The purposeful application of energy (e.g., electrical energy, thermal energy) to tissue by energy delivery element(s) can induce one or more desired thermal heating effects on localized regions of the renal artery and adjacent regions of the renal plexus, which lay intimately within or adjacent to the adventitia of the renal artery. The purposeful application of the thermal heating effects can achieve neuromodulation along all or a portion of the renal plexus.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity (RSNA) is expected.

II. Selected Embodiments of Neuromodulation Systems

FIG. 1 illustrates a renal neuromodulation system 10 ("system 10") configured in accordance with an embodiment of the present technology. The system 10 includes an intravascular catheter 12 operably coupled to an energy source or energy generator 26 (e.g., a RF energy generator). The catheter 12 can include an elongated shaft 16 having a proximal portion 18, a handle 34 at a proximal region of the proximal portion 18, and a distal portion 20. The catheter 12 can further include a therapeutic assembly or treatment section 21 (shown schematically) at the distal portion 20

(e.g., attached to the distal portion 20, defining a section of the distal portion 20, etc.). As explained in further detail below, the therapeutic assembly 21 can include a support structure 22 and an array of two or more energy delivery elements 24 (e.g., electrodes) configured to be delivered to a renal blood vessel (e.g., a renal artery) in a low-profile configuration. Upon delivery to the target treatment site within the renal blood vessel, the therapeutic assembly 21 is further configured to be deployed into an expanded state (e.g., a generally spiral/helical configuration) for delivering energy at the treatment site and providing therapeutically-effective electrically- and/or thermally-induced renal neuromodulation. Alternatively, the deployed state may be non-helical provided that the deployed state delivers the energy to the treatment site. The therapeutic assembly 21 may be transformed between the delivery and deployed states using a variety of suitable mechanisms or techniques (e.g., self-expansion, remote actuation via an actuator, etc.).

The proximal end of the therapeutic assembly 21 is carried by or affixed to the distal portion 20 of the elongated shaft 16. A distal end of the therapeutic assembly 21 may terminate the catheter 12 with, for example, an atraumatic tip 40. In some embodiments, the distal end of the therapeutic assembly 21 may also be configured to engage another element of the system 10 or catheter 12. For example, the distal end of the therapeutic assembly 21 may define a passageway for receiving a guide wire (not shown) for delivery of the treatment device using over-the-wire ("OTW") or rapid exchange ("RX") techniques. Further details regarding such arrangements are described below.

The catheter 12 can be electrically coupled to the energy source 26 via a cable 28, and the energy source 26 (e.g., a RF energy generator) can be configured to produce a selected modality and magnitude of energy for delivery to the treatment site via the energy delivery elements 24. As described in greater detail below, supply wires (not shown) can extend along the elongated shaft 16 or through a lumen in the shaft 16 to the individual energy delivery elements 24 and transmit the treatment energy to the energy delivery elements 24. In some embodiments, each energy delivery element 24 includes its own supply wire. In other embodiments, however, two or more energy delivery elements 24 may be electrically coupled to the same supply wire. A control mechanism 32, such as foot pedal or handheld remote control device, may be connected to the energy source 26 to allow the clinician to initiate, terminate and, optionally, adjust various operational characteristics of the energy source 26, including, but not limited to, power delivery. The remote control device (not shown) can be positioned in a sterile field and operably coupled to the energy delivery elements 24, and can be configured to allow the clinician to selectively activate and deactivate the energy delivery elements 24. In other embodiments, the remote control device may be built into the handle assembly 34.

The energy source or energy generator 26 can be configured to deliver the treatment energy via an automated control algorithm 30 and/or under the control of a clinician. For example, the energy source 26 can include computing devices (e.g., personal computers, server computers, tablets, etc.) having processing circuitry (e.g., a microprocessor) that is configured to execute stored instructions relating to the control algorithm 30. In addition, the processing circuitry may be configured to execute one or more evaluation/feedback algorithms 31, which can be communicated to the clinician. For example, the energy source 26 can include a monitor or display 33 and/or associated features that are configured to provide visual, audio, or other indications of power levels, sensor data, and/or other feedback. The energy source 26 can also be configured to communicate the feedback and other information to another device, such as a monitor in a catheterization laboratory.

Figure 2:
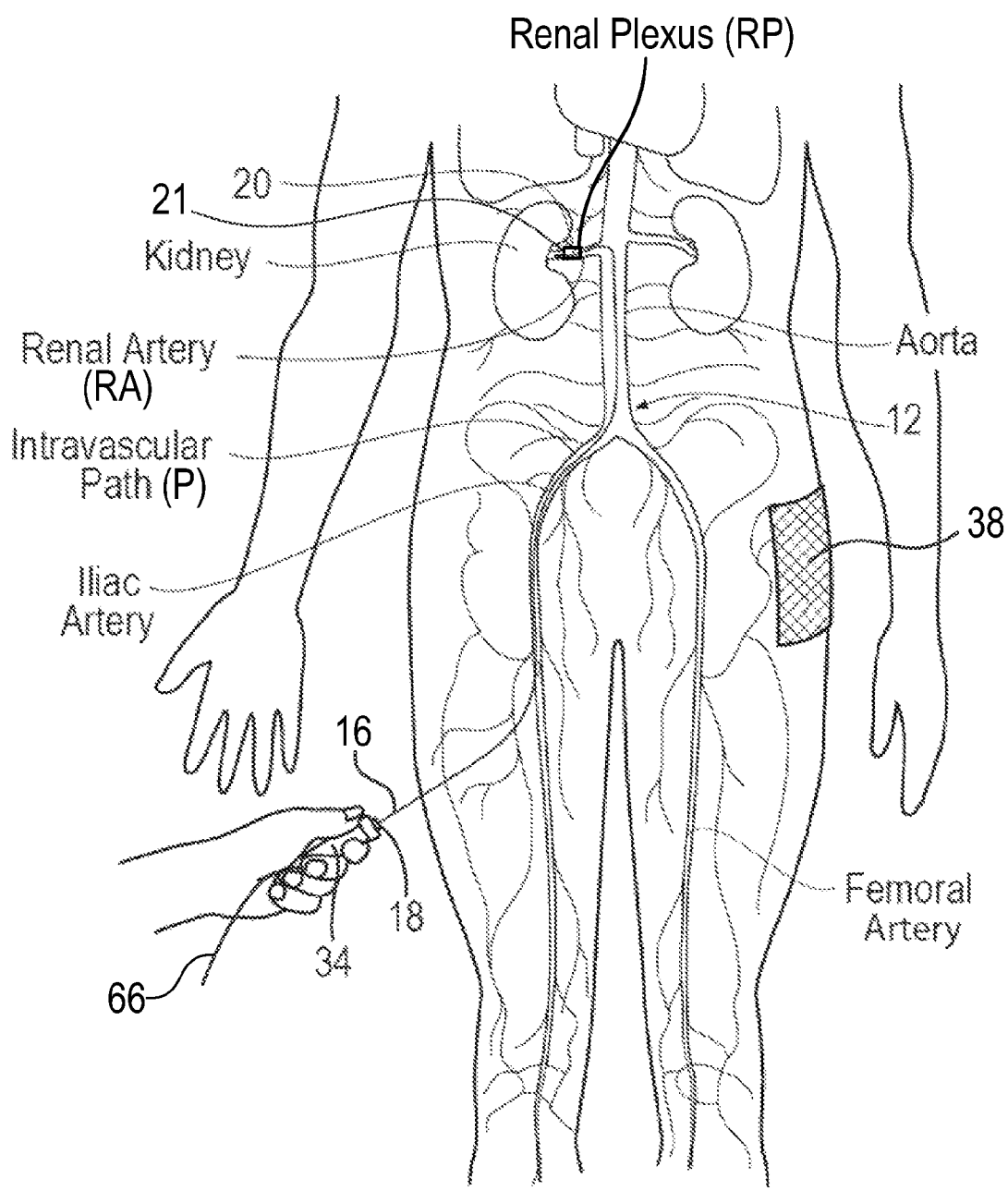
FIG. 2 illustrates modulating renal nerves with a multi-electrode catheter configured in accordance with an embodiment of the present technology.

The energy delivery elements 24 may be configured to deliver power independently (i.e., may be used in a monopolar fashion), either simultaneously, selectively, or sequentially, and/or may deliver power between any desired combination of the elements (i.e., may be used in a bipolar fashion). In monopolar embodiments, a neutral or dispersive electrode 38 may be electrically connected to the energy generator 26 and attached to the exterior of the patient (e.g., as shown in FIG. 2). Furthermore, the clinician optionally may choose which energy delivery element(s) 24 are used for power delivery in order to form highly customized lesion(s) within the renal artery having a variety of shapes or patterns. In still other embodiments, the system 10 can be configured to deliver other suitable forms of treatment energy, such as a combination of monopolar and bipolar electric fields.

In several embodiments, the energy source 26 may include a radio-frequency identification (RFID) evaluation module (not shown) mounted at or near one or more ports on the energy source 26 and configured to wirelessly read and write to one or more RFID tags (not shown) on the catheter 12. In one particular embodiment, for example, the catheter 12 may include an RFID tag housed within or otherwise attached to the connector portion of the cable 28 that is coupled to the energy source 26. The RFID tag can include, for example, an antenna and an RFID chip for processing signals, sending/receiving RF signals, and storing data in memory. Suitable RFID tags include, for example, MB89R118 RFID tags available from Fujitsu Limited of Tokyo, Japan. The memory portion of the RFID tag can include a plurality of blocks allocated for different types of data. For example, a first memory block can include a validation identifier (e.g., a unique identifier associated with the specific type of catheter and generated from the unique ID of the RFID tag using an encrypting algorithm), and a second memory block can be allocated as a catheter usage counter that can be read and then written to by the RFID module carried by the energy source 26 after catheter use. In other embodiments, the RFID tag can include additional memory blocks allocated for additional catheter usage counters (e.g., to allow the catheter 12 to be used a specific limited number of times) and/or other information associated with the catheter 12 (e.g., lot number, customer number, catheter model, summary data, etc.).

The RFID evaluation module carried by the energy source 26 can include an antenna and a processing circuit that are together used to communicate with one or more portions of the energy source 26 and wirelessly read/write to one or more RFID tag within its proximity (e.g., when the cable 28 including an RFID tag is attached to the energy source 26). Suitable RFID evaluation modules include, for example, a TRF7960A Evaluation Module available from Texas Instruments Incorporated of Dallas, Texas.

In operation, the RFID evaluation module is configured to read information from the RFID tag (carried by the cable 28 or another suitable portion of the catheter 12), and communicate the information to software of the energy source 26 to validate the attached catheter 12 (e.g., validate that the catheter 12 is compatible with the energy source 26), read the number of previous uses associated with the particular catheter 12, and/or write to the RFID tag to indicate catheter use. In various embodiments, the energy source 26 may be configured to disable energy delivery to the catheter 12 when predefined conditions of the RFID tag are not met. For example, when each the catheter 12 is connected to the energy source 26, the RFID evaluation module can read a unique anti-counterfeit number in an encrypted format from the RFID tag, decrypt the number, and then authenticate the number and the catheter data format for recognized catheters (e.g., catheters that are compatible with the particular energy source 26, non-counterfeit catheters, etc.). In various embodiments, the RFID tag can include identifier(s) that correspond to a specific type of catheter, and the RFID evaluation module can transmit this information to a main controller of the energy source 26, which can adjust the settings (e.g., the control algorithm 30) of the energy source 26 to the desired operating parameters/characteristics (e.g., power levels, display modes, etc.) associated with the specific catheter. Further, if the RFID evaluation module identifies the catheter 12 as counterfeit or is otherwise unable to identify the catheter 12, the energy source 26 can automatically disable the use of the catheter 12 (e.g., preclude energy delivery).

Once the catheter 12 has been identified, the RFID evaluation module can read the RFID tag memory address spaces to determine if the catheter 12 was previously connected to a generator (i.e., previous used). In certain embodiments, the RFID tag may limit the catheter 12 to a single use, but in other embodiments the RFID tag can be configured to provide for more than one use (e.g., 2 uses, 5 uses, 10 uses, etc.). If the RFID evaluation module recognizes that the catheter 12 has been written (i.e., used) more than a predetermined use limit, the RFID module can communicate with the energy source 26 to disable energy delivery to the catheter 12. In certain embodiments, the RFID evaluation module can be configured to interpret all the catheter connections to an energy source within a predefined time period (e.g., 5 hours, 10 hours, 24 hours, 30 hours, etc.) as a single connection (i.e., a single use), and allow the catheter 12 to be used multiple times within the predefined time period. After the catheter 12 has been detected, recognized, and judged as a "new connection" (e.g., not used more than the predefined limit), the RFID evaluation module can write to the RFID tag (e.g., the time and date of the system use and/or other information) to indicate that the catheter 12 has been used. In other embodiments, the RFID evaluation module and/or RFID tag may have different features and/or different configurations.

The system 10 can also include one or more sensors (not shown) located proximate to or within the energy delivery elements 24. For example, the system 10 can include temperature sensors (e.g., thermocouple, thermistor, etc.), impedance sensors, pressure sensors, optical sensors, flow sensors, and/or other suitable sensors connected to one or more supply wires (not shown) that transmit signals from the sensors and/or convey energy to the energy delivery elements 24. FIG. 2 (with additional reference to FIG. 1) illustrates modulating renal nerves with an embodiment of the system 10. The catheter 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. In the embodiment illustrated in FIG. 2, the therapeutic assembly 21 is delivered intravascularly to the treatment site using a guide wire 66 in an OTW technique. As noted previously, the distal end of the therapeutic assembly 21 may define a lumen or passageway for receiving the guide wire 66 for delivery of the catheter 12 using either OTW or RX techniques. At the treatment site, the guide wire 66 can be at least partially axially withdrawn or removed, and the therapeutic assembly 21 can transform or otherwise be moved to a deployed arrangement for delivering energy at the treatment site. Further details regarding such arrangements are described below with reference to FIGS. 3A and 3B. The guide wire 66 may comprise any suitable medical guide wire sized to slidably fit within the lumen. In one particular embodiment, for example, the guide wire 66 may have a diameter of 0.356 mm (0.014 inch). In other embodiments, the therapeutic assembly 21 may be delivered to the treatment site within a guide sheath (not shown) with or without using the guide wire 66. When the therapeutic assembly 21 is at the target site, the guide sheath may be at least partially withdrawn or retracted and the therapeutic assembly 21 can be transformed into the deployed arrangement. Additional details regarding this type of configuration are described below. In still other embodiments, the shaft 16 may be steerable itself such that the therapeutic assembly 21 may be delivered to the treatment site without the aid of the guide wire 66 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the therapeutic assembly 21. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the catheter 12. Further, in some embodiments, image guidance components (e.g., IVUS, OCT) may be integrated with the catheter 12 and/or run in parallel with the catheter 12 to provide image guidance during positioning of the therapeutic assembly 21. For example, image guidance components (e.g., IVUS or OCT) can be coupled to at least one of the therapeutic assembly 21 (e.g., proximal to the therapeutic arms 25) to provide three-dimensional images of the vasculature proximate the target site to facilitate positioning or deploying the multi-electrode assembly within the target renal blood vessel.

The purposeful application of energy from the energy delivery elements 24 may then be applied to target tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements 24 (FIG. 1) and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Figure 3B:
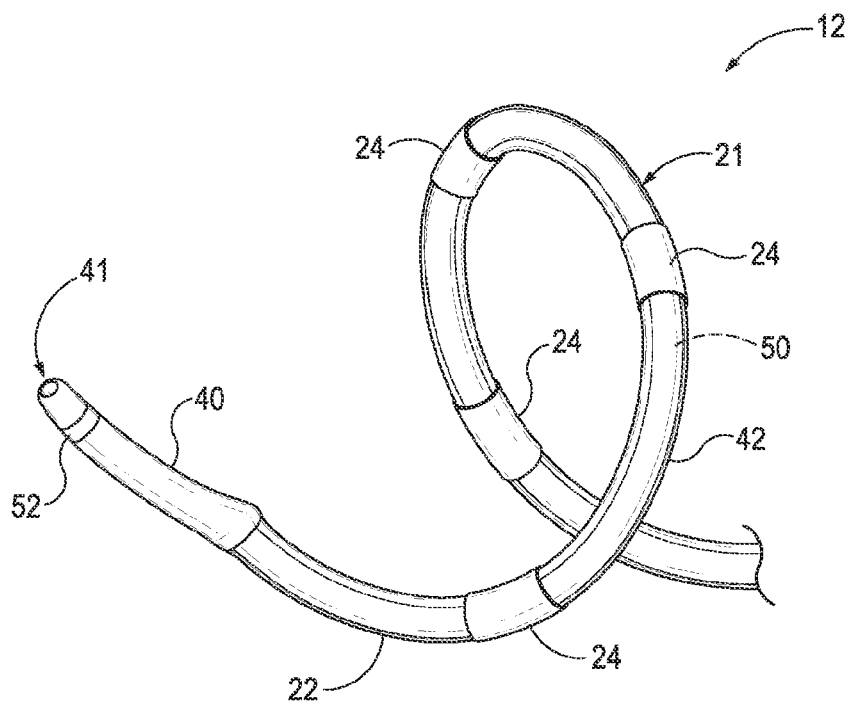
FIG. 3B is a perspective view of the distal portion of the catheter of FIG. 3A in a deployed state (e.g., expanded configuration) outside the patient.

FIG. 3A is a side view of the distal portion 20 of the catheter 12 and the therapeutic assembly or treatment section 21 in a delivery state (e.g., low-profile or collapsed configuration) outside a patient, and FIG. 3B is a perspective view of the therapeutic assembly 21 in a deployed state (e.g., expanded configuration) outside the patient. As described previously, the catheter 12 may be configured for OTW delivery from an access site in which the guide wire 66 (FIG. 2) is initially inserted to a treatment site (e.g., within a renal artery), and the catheter 12 is installed over the guide wire. As described in greater detail below, a guide wire may be either inserted into or at least partially withdrawn from the distal portion 20 to transform the therapeutic assembly 21 between the delivery state (FIG. 3A) and the deployed state (FIG. 3B). For example, as shown in FIG. 3A, a guide wire (not shown) extending through at least a portion of the length of the catheter 12 may be configured to straighten a pre-shaped spiral/helical control member 50 (shown schematically in broken lines) of the catheter 12 during delivery, and the guide wire may be at least partially withdrawn or slidably moved relative to the distal portion 20 to allow the therapeutic assembly 21 to transform to the deployed state (FIG. 3B).

As best seen in FIG. 3A, the therapeutic assembly 21 includes multiple (e.g., four, five, etc.) energy delivery elements 24 carried by the support structure 22. In this embodiment, the support structure 22 comprises a flexible tube 42 and the pre-shaped control member 50 within the tube 42. The flexible tube 42 may be composed of a polymer material such as polyamide, polyimide, polyether block amide copolymer sold under the trademark PEBAX, polyethylene terephthalate (PET), polypropylene, aliphatic, polycarbonate-based thermoplastic polyurethane sold under the trademark CARBOTHANE, or a polyether ether ketone (PEEK) polymer that provides the desired flexibility. In other embodiments, however, the tube 42 may be composed of other suitable materials.

As mentioned above, the pre-shaped control member 50 may be used to provide a spiral/helical shape to the relatively flexible distal portion 20 of the catheter 12. As best seen in FIG. 3B, for example, the control member 50 is a tubular structure comprising a nitinol multifilar stranded wire with a lumen therethrough and sold under the trademark HELICAL HOLLOW STRAND (HHS), and commercially available from Fort Wayne Metals of Fort Wayne, Indiana. The tubular control member 50 may be formed from a variety of different types of materials, may be arranged in a single or dual-layer configuration, and may be manufactured with a selected tension, compression, torque and pitch direction. The HHS material, for example, may be cut using a laser, electrical discharge machining (EDM), electrochemical grinding (ECG), or other suitable means to achieve a desired finished component length and geometry. For example, as best seen in FIG. 3B, the control member 50 in the present embodiment has a pre-set spiral/helical configuration that defines the deployed state of the therapeutic assembly 21 such that the energy delivery elements 24 of the therapeutic assembly 21 are offset from each other (e.g., both angularly and longitudinally offset relative to a longitudinal axis of the renal artery) and may be positioned in stable apposition with a wall of the renal artery (FIG. 2) for treatment. For purposes of clarification, the pre-set helical shape of the therapeutic assembly 21 in its deployed state may be defined by dimensions (e.g., helix diameter and pitch) that are distinct from the dimensions (e.g., helix diameter and pitch) of the HHS itself. In other words, the multifilar hollow tube forming control member 50 is itself pre-set into a helical shape.

Figure 4:
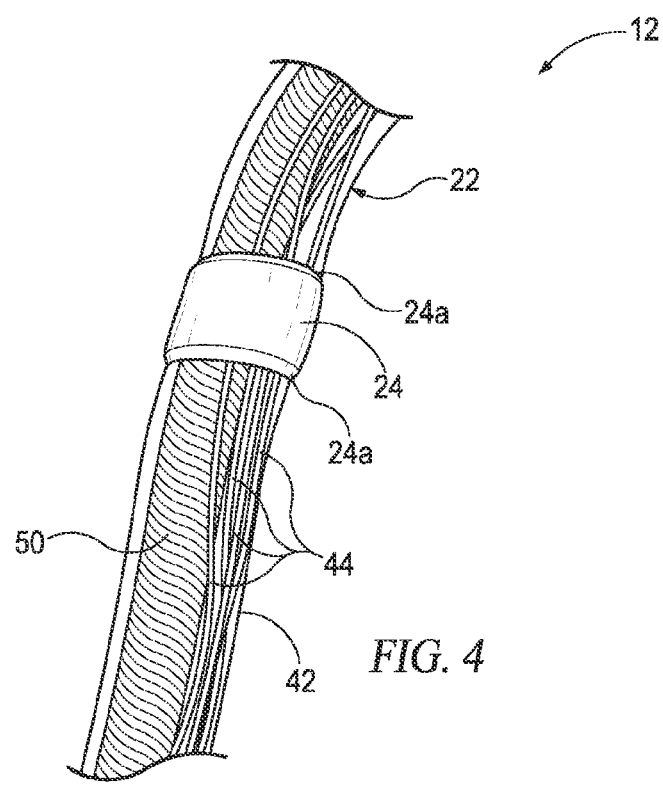
FIG. 4 is an enlarged view of a portion of the treatment device of FIG. 3A.

Forming the control member 50 of nitinol multifilar stranded wire(s) or other similar materials is expected to eliminate the need for any additional reinforcement wire(s) or structures within the support structure 22 to provide a desired level of support and rigidity to the therapeutic assembly 21. This feature is expected to reduce the number of manufacturing processes required to form the catheter 12 and reduce the number of materials required for the device. Another feature of the therapeutic assembly 21 is that the control member 50 and inner wall of the tube 42 are in intimate contact and there is little or no space between the control member 50 and the tube 42 (as best seen in FIG. 4). In one embodiment, for example, tube 42 can be expanded prior to assembly such that applying hot air to the tube 42 during the manufacturing process can shrink the tube onto the control member 50, as will be understood by those familiar with the ordinary use of shrink tubing materials. This feature is expected to inhibit or eliminate wrinkles or kinks that might occur in the tube 42 as the therapeutic assembly 21 transforms from the relatively straight delivery state to the deployed, generally helical state.

In other embodiments, the control member 50 and/or other components of the support structure 22 may be composed of different materials and/or have a different arrangement. For example, the control member 50 may be formed from other suitable shape memory materials (e.g., nickel-titanium (nitinol), wire or tubing besides HHS, shape memory polymers, electro-active polymers) that are pre-formed or pre-shaped into the desired deployed state. Alternatively, the control member 50 may be formed from multiple materials such as a composite of one or more polymers and metals.

The array of energy delivery elements 24 can include series of separate band electrodes spaced along the support structure 22 and bonded to the tube 42 using an adhesive. Band or tubular electrodes may be used in some embodiments, for example, because they typically have lower power requirements for ablation as compared to disc or flat electrodes. In other embodiments, however, disc or flat electrodes are also suitable. In still another embodiment, electrodes having a spiral or coil shape may be utilized. In some embodiments, the energy delivery elements 24 may be equally spaced apart along the length of the support structure 22. The energy delivery elements 24 may be formed from any suitable metallic material (e.g., gold, platinum, an alloy of platinum and iridium, etc.). In other embodiments, however, the number, arrangement, and/or composition of the energy delivery elements 24 may vary.

FIG. 4 is an enlarged view of a portion of the catheter 12 of FIG. 3A. Referring to FIGS. 1 and 4 together, each energy delivery element or electrode 24 is electrically connected to the energy source 26 (FIG. 1) by a conductor or bifilar wire 44 extending through a lumen of the tube 42. Each energy delivery element 24 may be welded or otherwise electrically coupled to its energy supply wire 44, and each wire 44 can extend through the tube 42 and elongated shaft 16 (FIG. 1) for the entire length of the shaft such that a proximal end thereof is coupled to the energy source 26 (FIG. 1). As noted above, the tube 42 is configured to fit tightly against the control member 50 and wires 44 to minimize the space between an inner portion of the tube 42 and the components positioned therein to help prevent the formation of wrinkles in the therapeutic assembly 21 during deployment. In some embodiments, the catheter 12 may also include an insulating layer (e.g., a layer of PET or another suitable material) over the control member 50 to further electrically isolate the material (e.g., HHS) of the control member 50 from the wires 44.

As best seen in FIG. 4, each energy delivery element 24 may include tapered end portions 24a (e.g., fillets) configured to provide an obtuse angle between an outer surface of the tube 42 and an outer surface of the corresponding energy delivery element 24. The smooth transition in angle provided by the tapered end portions 24a is expected to help prevent a guide sheath or loading tool from getting stuck or catching the edges of the energy delivery elements 24 as the guide sheath or loading tool is moved over the length of the therapeutic assembly 21 (FIGS. 3A and 3B) during advancement and retrieval. In other embodiments, the extent of the tapered portions 24a on the energy delivery elements 24 may vary. In some embodiments, the tapered end portions 24a comprise fillets formed from adhesive material at either end of the corresponding energy delivery elements 24. In other embodiments, however, the tapered end portions 24a may be formed from the same material as the tube 42 (e.g., integrally formed with the tube 42 or formed separately and attached to either end of corresponding energy delivery elements 24). Further, the tapered portions 24a are an optional feature that may not be included in some embodiments.

Referring back to FIGS. 3A and 3B, the therapeutic assembly 21 includes the atraumatic, flexible curved tip 40 at a distal end of the assembly 21. The curved tip 40 is configured to provide a distal opening 41 for the guide wire 66 (FIG. 2) that directs the guide wire away from the wall of the renal artery when the therapeutic assembly 21 is in the pre-set deployed configuration. This feature is expected to facilitate alignment of the helical therapeutic assembly 21 in the renal blood vessel as it expands, while also reducing the risk of injuring the blood vessel wall when the guide wire distal tip is advanced from the opening 41. The curvature of the tip 40 can be varied depending upon the particular sizing/configuration of the therapeutic assembly 21. As best seen in FIG. 3B, for example, in the illustrated embodiment the tip 40 is curved such that it is off the pre-set spiral/helical axis defined by the control member 50. In other embodiments, however, the tip 40 may have a different curvature. In some embodiments, the tip 40 may also comprise one or more radiopaque markers 52 and/or one or more sensors (not shown). The tip 40 can be affixed to the distal end of the support structure 22 via adhesive, crimping, over-molding, or other suitable techniques.

The flexible curved tip 40 can be made from a polymer material (e.g., polyether block amide copolymer sold under the trademark PEBAX), a thermoplastic polyether urethane material (sold under the trademarks ELASTHANE or PELLETHANE), or other suitable materials having the desired properties, including a selected durometer. As noted above, the tip 40 is configured to provide an opening for the guide wire 66, and it is desirable that the tip itself maintain a desired shape/configuration during operation. Accordingly, in some embodiments, one or more additional materials may be added to the tip material to help improve tip shape retention. In one particular embodiment, for example, about 5 to 30 weight percent of siloxane can be blended with the tip material (e.g., the thermoplastic polyether urethane material), and electron beam or gamma irradiation may be used to induce cross-linking of the materials. In other embodiments, the tip 40 may be formed from different material(s) and/or have a different arrangement.

In operation (and with reference to FIGS. 2, 3A, and 3B), after positioning the therapeutic assembly 21 at the desired location within the renal artery RA of the patient, the therapeutic assembly 21 may be transformed from its delivery state to its deployed state or deployed arrangement. The transformation may be initiated using an arrangement of device components as described herein with respect to the particular embodiments and their various modes of deployment. In one embodiment, for example, the therapeutic assembly 21 may be deployed by retracting the guide wire 66 until a distal tip of the guide wire 66 is generally aligned with the tip 40 of the catheter 12. In some embodiments, the guide wire 66 may have a varying stiffness or flexibility along its length so as to provide increased flexibility distally. When the varying flexible guide wire 66 is partially retracted as described above, the pre-set helical shape of the control member 50 provides a shape-recovery force sufficient to overcome the straightening force provided by the distalmost portion of the guide wire 66 such that the therapeutic assembly 21 can deploy into its helical configuration. Further, because the flexible distal portion of the guide wire 66 remains within the therapeutic assembly 21 in the deployed state, the guide wire 66 can impart additional structural integrity to the helically-shaped portion during treatment. This feature is expected to help mitigate or reduce problems associated with keeping the therapeutic assembly 21 in place during treatment (e.g., help with vasoconstriction).

In another embodiment, the guide wire 66 may have a stiffness profile that permits the distal portion of the guide wire 66 to remain extended from the opening 41 while still permitting the therapeutic assembly 21 to transform to its deployed configuration. In still other embodiments, the guide wire 66 may be withdrawn completely from the therapeutic assembly 21 (e.g., a distalmost end portion of the guide wire 66 is proximal of the therapeutic assembly 21) to permit the transformation, while a distalmost portion of the guide wire 66 remains within the shaft 16. In yet another embodiment, the guide wire 66 may be withdrawn completely from the shaft 16. In any of the foregoing examples, the clinician can withdraw the guide wire 66 sufficiently to observe transformation of the therapeutic assembly 21 to the deployed configuration and/or until an X-ray image shows that the distal tip of the guide wire 66 is at a desired location relative to the therapeutic assembly 21 (e.g., generally aligned with the tip 40, completely withdrawn from the therapeutic assembly 21, etc.). In some embodiments, the extent of withdrawal for the guide wire 66 can be based, at least in part, on the clinician's judgment with respect to the selected guide wire and the extent of withdrawal necessary to achieve deployment.

After treatment, the therapeutic assembly 21 may be transformed back to the low-profile delivery configuration by axially advancing the guide wire 66 relative to the therapeutic assembly 21. In one embodiment, for example, the guide wire 66 may be advanced until the distal tip of the guide wire 66 is generally aligned with the tip 40, and the catheter 12 can then be pulled back over the stationary guide wire 66. In other embodiments, however, the distalmost portion of the guide wire 66 may be advanced to different location relative to the therapeutic assembly 21 to achieve transformation of the therapeutic assembly 21 back to low-profile arrangement.

The embodiments of the catheter systems described above include a procedural guide wire to guide the catheter to the treatment site and also to restrain the therapeutic assembly or treatment section in a low-profile delivery state. In further embodiments, catheter systems configured in accordance with the present technology may further include an external loading tool that can be disposed and retracted over the therapeutic assembly to further assist with transforming the therapeutic assembly between the delivery and deployed configurations.

Figure 5:
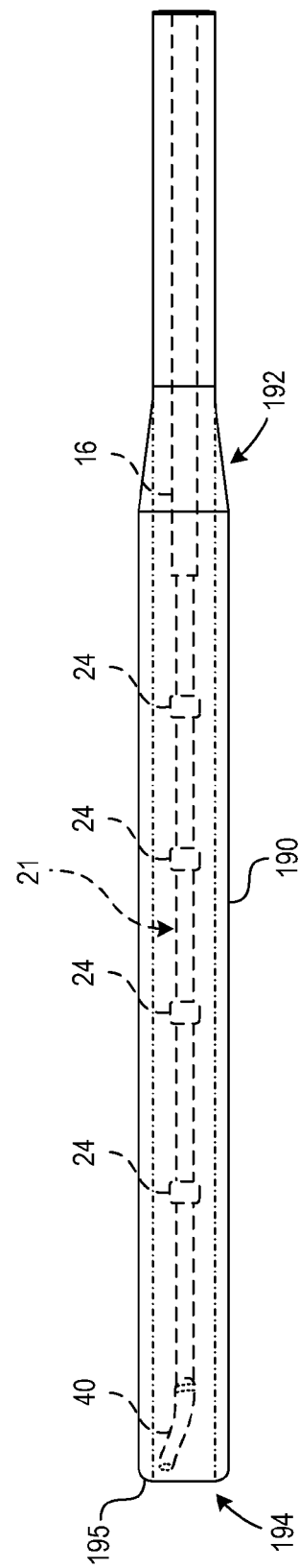
FIG. 5 is a partially schematic side view of a loading tool configured in accordance with an embodiment of the present technology.

FIG. 5, for example, is a partially schematic side view of a loading tool 190 in accordance with an embodiment of the present technology. The loading tool 190 is a tubular structure configured to slidably move along an outer surface of the shaft 16 and the therapeutic assembly 21 (for purposes of illustration, the therapeutic assembly 21 and associated features are shown in broken lines). The loading tool 190 has a size and stiffness suitable for maintaining the therapeutic assembly 21 in the low-profile configuration for backloading of the guide wire 66 (FIG. 2), i.e., insertion of the proximal end of guide wire 66 into the distal opening 41. In the illustrated embodiment, the loading tool 190 can include a tapered portion 192 to help facilitate advancement of the sheath over the therapeutic assembly 21 and the associated energy delivery elements 24. In some embodiments, a distal portion 194 of the loading tool 190 may also include smooth, rounded inner and outer edges 195 to help ease the inner wall of the loading tool over the energy delivery elements 24 during advancement of the loading tool relative to the therapeutic assembly 21. The loading tool 190 may be composed of high-density polyethylene (HDPE) or other suitable materials having a desired strength and lubricity. In still other embodiments, the loading tool 190 may be composed of two or more different materials. In one embodiment, for example, the larger diameter section of the loading tool 190 distal of the tapered portion 192 may be composed of HDPE, while the smaller diameter section of the loading tool 190 proximal of the tapered portion 192 may be composed of linear low-density polyethylene (LLDPE). In still further embodiments, the loading tool 190 may be composed of different materials and/or have a different arrangement.

In some embodiments, the loading tool 190 may be used in conjunction with the catheter 12 while the catheter 12 is external to the patient before treatment, and then removed from the catheter 12 before the catheter 12 is inserted into the patient. More specifically, as discussed above, the loading tool 190 can be used to maintain the therapeutic assembly 21 in the low-profile configuration while the guide wire is backloaded (moving from a distal end toward a proximal end of the catheter 12). The loading tool 190 can then be removed from the catheter 12, and the therapeutic assembly 21 can be restrained in the delivery configuration with the support of the guide wire. In another embodiment, the loading tool 190 may remain installed on the catheter 12 after backloading of the guide wire, but may be slid down the length of the catheter 12 to a proximal portion 18 of the catheter 12 near the handle 34 (FIG. 1). In this way, the loading tool 190 remains with the catheter 12, but is out of the way during treatment.

In still other embodiments, however, the loading tool 190 may remain at or near the distal portion 20 (FIG. 1) of the catheter 12 during treatment. For example, in one embodiment, a clinician may keep the loading tool 190 at or near the distal portion 20 of the catheter 12 and then insert the loading tool 190 into a hemostasis valve (not shown) connected to a guide catheter (not shown). Depending upon a profile of the loading tool 190 and an inner diameter of the hemostasis valve, the clinician may be able to insert approximately 2 to 4 cm of the loading tool 190 into the hemostasis valve. One advantage of this approach is that the therapeutic assembly 21 (FIGS. 3A and 3B) is further protected as the catheter 12 is advanced through the hemostasis valve, and the clinician is expected to feel little or no friction between the catheter 12 and the hemostasis valve. In other embodiments, however, the loading tool 190 may have a different arrangement relative to the hemostasis valve and/or the other components of the system 10 (FIG. 1) during operation.

III. Further Examples

The following examples are illustrative of several embodiments of the present technology:

1. A catheter apparatus, comprising:
   an elongated tubular shaft having a proximal portion and a distal portion; and
   a therapeutic assembly disposed at the distal portion of the elongated shaft and adapted to be located at a target location within a renal artery of a human patient, the therapeutic assembly including a support structure comprising—
      a control member comprising a pre-formed helical shape, wherein the control member is a tubular structure having a lumen therethrough and is composed of a nitinol multifilar stranded wire; and
      a plurality of energy delivery elements carried by the support structure,
   wherein the elongated tubular shaft and the therapeutic assembly together define therethrough a guide wire lumen configured to slidably receive a medical guide wire, and
   wherein axial movement of the guide wire relative to the therapeutic assembly transforms the support structure between (a) a low-profile delivery configuration and (b) a deployed configuration tending to assume the pre-formed helical shape of the control member.

2. The catheter apparatus of example 1 wherein the therapeutic assembly is configured to transform between the low-profile delivery configuration and the deployed configuration while at least a distal portion of the guide wire remains in the guide wire lumen of the therapeutic assembly.

3. The catheter apparatus of example 2 wherein the support structure comprises a shape-recovery force sufficient to overcome a straightening force provided by a distal region of the guide wire to transform the therapeutic assembly to the deployed configuration when a distalmost tip of the guide wire is generally aligned with a distal tip of the therapeutic assembly.

4. The catheter apparatus of example 1 wherein:
   the support structure comprises a shape-recovery force insufficient to overcome a straightening force provided by a distal region of the guide wire when the guide wire is within the guide wire lumen of the therapeutic assembly; and
   the therapeutic assembly is configured to transform to the deployed configuration when a distalmost portion of the guide wire is withdrawn though the guide wire lumen to a point proximal of the therapeutic assembly.

5. The catheter apparatus of any one of examples 1 to 4 wherein a distal portion of the therapeutic assembly further comprises a flexible curved tip configured to provide an opening for the guide wire and, in the deployed configuration, to direct the guide wire away from a wall of the renal artery.

6. The catheter apparatus of example 5 wherein the flexible curved tip is composed of polyether block amide copolymer.

7. The catheter apparatus of example 5 wherein the flexible curved tip is composed of a thermoplastic polyether urethane material.

8. The catheter apparatus of example 7 wherein the flexible curved tip is composed of about 5 to 30 weight percent of siloxane blended with the thermoplastic polyether urethane material.

9. The catheter apparatus of any one of examples 1 to 8 wherein, in the deployed configuration, the energy delivery elements carried by the support structure are spaced apart from each other along a longitudinal axis of the renal artery and are configured to maintain apposition with a wall of the renal artery.

10. The catheter apparatus of any one of examples 1 to 9 wherein the energy delivery elements comprise a series of band electrodes.

11. The catheter apparatus of example 10 wherein at least one of the band electrodes comprises tapered end portions, and wherein the tapered end portions are configured to provide an obtuse angle between an outer surface of the support structure and an outer surface of the at least one band electrode.

12. The catheter apparatus of any one of examples 1 to 11 wherein the therapeutic assembly comprises four energy delivery elements.

13. The catheter apparatus of any one of examples 1 to 12, further comprising a retractable loading tool surrounding and restraining at least a longitudinal portion of the therapeutic assembly in the low-profile delivery configuration.

14. The catheter apparatus of example 13 wherein the loading tool comprises a distal end portion having rounded edges.

15. A renal neuromodulation system for treatment of a human patient, the system comprising:
an elongate shaft having a proximal end and a distal end, wherein the distal end of the shaft is configured for intravascular delivery over a procedural guide wire to a renal artery of the patient;
a pre-shaped tubular spiral structure disposed at or proximate to the distal end of the elongate shaft, wherein the spiral structure is configured to transform between an unexpanded configuration and an expanded configuration that tends to assume the shape of the pre-shaped spiral structure, and wherein the spiral structure is composed, at least in part, of multifilar stranded nitinol wire; and
a plurality of electrodes associated with the spiral structure,
wherein the elongate shaft and the spiral structure together define a guide wire lumen therethrough, and wherein—
the guide wire lumen is configured to slidably receive the procedural guide wire to locate the spiral structure at a target treatment site within a renal blood vessel of the patient and to restrain the spiral structure in the unexpanded configuration, and wherein
proximal movement of the procedural guide wire through the guide wire lumen relative to the spiral structure such that a distal end portion of the guide wire is at least partially within the guide wire lumen transforms the spiral structure to the expanded configuration.

16. The system of example 15 wherein the procedural guide wire comprises a distal portion having varying flexibility, and further wherein at least a region of the distal portion of the guide wire is configured to remain within the portion of the guide wire lumen defined by the spiral structure when the spiral structure is in the expanded configuration.

17. The system of example 15 or example 16, further comprising a flexible tube covering and in intimate contact with the spiral structure.

18. The system of example 17 wherein the plurality of electrodes are bonded to the flexible tube using an adhesive material.

19. The system of any one of examples 15 to 18 wherein the plurality of electrodes are composed of gold.

20. The system of any one of examples 15 to 19 wherein the plurality of electrodes are individually connectable to an energy source external to the patient, and wherein the energy source is capable of individually controlling the energy delivered to each electrode during therapy.

21. A method of performing renal neuromodulation, the method comprising:
intravascularly delivering a renal neuromodulation catheter in a low-profile delivery configuration over a guide wire to a target treatment site within a renal blood vessel of a human patient and at least proximate to a renal nerve of the patient, wherein the renal neuromodulation catheter comprises—an elongated shaft; and
a multi-electrode array disposed at a distal portion of the shaft and composed, at least in part, of a tubular structure formed of multifilar nitinol wire;
withdrawing the guide wire in a proximal direction until the catheter transforms from the low-profile delivery configuration to a deployed configuration wherein the tubular structure has a radially expanded, generally spiral shape configured to contact the wall of the renal blood vessel and to allow blood to flow through the vessel; and
selectively delivering energy to one or more electrodes of the multi-electrode array to inhibit neural communication along the renal nerve.

22. The method of example 21 wherein selectively delivering energy to one or more electrodes of the multi-electrode array comprises producing a plurality of lesions in a desired pattern along the renal blood vessel.

23. The method of example 21 or example 22 wherein the individual electrodes of the multi-electrode array are spaced sufficiently apart such that the lesions do not overlap.

24. The method of any one of examples 21 to 23, further comprising attaching an external ground to an exterior of the patient, and wherein selectively delivering energy to one or more electrodes further comprises delivering an electric field in a monopolar fashion between each of the electrodes and the external ground.

25. The method of any one of examples 21 to 23 wherein selectively delivering energy comprises selectively delivering an electric field in a bipolar fashion between the electrodes of the multi-electrode array.

26. The method of any one of examples 21 to 25 wherein withdrawing the guide wire in a proximal direction until the therapeutic assembly transforms comprises only partially withdrawing the guide wire from the therapeutic assembly such that at least a portion of the guide wire remains in the therapeutic assembly after the therapeutic assembly transforms to the deployed configuration.

27. The method of any one of examples 21 to 25 wherein withdrawing the guide wire in a proximal direction until the therapeutic assembly transforms comprises completely withdrawing the guide wire from the therapeutic assembly such that a distalmost portion of the guide wire is withdrawn to a point proximal of the therapeutic assembly.

28. The method of any one of examples 21 to 27 wherein the target treatment site comprises a first target treatment site, and wherein the method further comprises:

advancing the guide wire in a distal direction after selectively delivering energy to the one or more electrodes of the multi-electrode array to transform the multi-electrode array from the deployed configuration back to the low-profile delivery configuration;

repositioning the catheter at a second target treatment site different than the first treatment site;

withdrawing the guide wire in a proximal direction to again transform the therapeutic assembly from the delivery configuration to the deployed configuration; and selectively delivering energy to one or more electrodes of the multi-electrode array positioned at the second target treatment site.

IV. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A renal denervation catheter for treatment of a human patient, the renal denervation catheter comprising:

a shaft having a proximal end and a distal end, wherein the distal end of the shaft is configured for intravascular delivery over a guide wire to a renal blood vessel of the patient;

a pre-shaped helical structure disposed at or proximate to the distal end of the shaft, wherein the helical structure is configured to transform between a low-profile delivery state and a deployed state tending to assume the shape of the pre-shaped helical structure, and wherein the helical structure is composed, at least in part, of nitinol; and a plurality of energy delivery elements carried by the helical structure, wherein the shaft and the helical structure together define a guide wire lumen therethrough, and wherein— the guide wire lumen is configured to slidably receive the guide wire to locate the helical structure at a target treatment site within the renal blood vessel of the patient and to restrain the helical structure in the low-profile delivery state, and the helical structure is reversibly transformable from the delivery state to the deployed state by proximally moving the guide wire through the guide wire lumen until a distalmost end of the guide wire is disposed within the helical structure.

2. The renal denervation catheter of claim 1 wherein:

the plurality of energy delivery elements are individually connectable to an energy source external to the patient; and the energy source is capable of individually controlling the energy delivered to each energy delivery element during therapy.

3. The renal denervation catheter of claim 1 wherein the plurality of energy delivery elements are composed of gold.

4. The renal denervation catheter of claim 1 wherein the plurality of energy delivery elements comprise a series of band electrodes.

5. The renal denervation catheter of claim 4 wherein at least one of the band electrodes comprises tapered end portions, and wherein the tapered end portions are configured to provide an obtuse angle between an outer surface of the support structure and an outer surface of the at least one band electrode.

6. The renal denervation catheter of claim 1 wherein the plurality of energy delivery elements comprise four electrodes carried by the helical structure.

7. The renal denervation catheter of claim 1 wherein the helical structure is configured to transform between the delivery state and the deployed state while at least the distalmost end of the guide wire is within the guide wire lumen and is disposed within the helical structure.

8. The renal denervation catheter of claim 1 wherein the helical structure comprises a shape-recovery force sufficient to overcome a straightening force provided by a distal region of the guide wire to transform the helical structure to the deployed state when the distalmost end of the guide wire is generally aligned with a distal tip of the helical structure.

9. The renal denervation catheter of claim 1 wherein a distal portion of the helical structure further comprises a flexible curved tip terminating in an open distal end of the guide wire lumen such that, when the helical structure is in the deployed state and the distalmost end of the guide wire is advanced from the open distal end, the guide wire distalmost end is directed away from a wall of the renal blood vessel.

10. The renal denervation catheter of claim 9 wherein the flexible curved tip is composed of polyether block amide copolymer.

11. The renal denervation catheter of claim 9 wherein the flexible curved tip is composed of a thermoplastic polyether urethane material.

12. The renal denervation catheter of claim 1 wherein the helical structure is composed, at least in part, of a nitinol multifilar stranded wire.

13. A method of treating a hypertensive human patient, the method comprising:
    transluminally delivering a renal neuromodulation catheter over a guide wire to a target treatment site within a renal artery of the patient, wherein the catheter comprises—
    a shaft; and
    a multi-electrode array at a distal region of the shaft, the multi-electrode array comprising a support structure composed, at least in part, of nitinol;
    proximally withdrawing the guide wire to transform the multi-electrode array from a low-profile delivery state to a deployed state in which the support structure has a radially expanded, generally spiral form shaped and sized to contact the wall of the renal artery and to allow blood to flow in and around the array; and
    selectively delivering radio-frequency (RF) energy from one or more electrodes of the multi-electrode array to renal nerves along the renal artery of the patient, thereby at least partially blocking neural traffic to and/or from a kidney of the patient.

14. The method of claim 13 wherein proximally withdrawing the guide wire to transform the multi-electrode array comprises partially withdrawing the guide wire from the multi-electrode array such that at least a portion of the guide wire remains in the multi-electrode array after the multi-electrode array transforms to the deployed state.

15. The method of claim 13 wherein proximally withdrawing the guide wire to transform the multi-electrode array comprises completely withdrawing the guide wire from the multi-electrode array such that a distalmost end of the guide wire is withdrawn to a point proximal of the multi-electrode array.

16. The method of claim 13 wherein selectively delivering RF energy from one or more electrodes of the multi-electrode array comprises selectively delivering RF energy in a bipolar fashion between the electrodes of the multi-electrode array.

17. The method of claim 13 wherein selectively delivering RF energy from one or more electrodes of the multi-electrode array comprises delivering RF energy in a monopolar fashion between a selected electrode and an external ground pad attached to skin of the patient.

18. The method of claim 13, further comprising monitoring a parameter of the one or more electrodes and/or tissue proximate to the renal nerves within the patient during therapy.

19. The method of claim 18 wherein monitoring a parameter comprises monitoring temperature and/or impedance.

20. The method of claim 18, further comprising controlling the delivery of RF energy from one or more electrodes to the renal nerves in response to the monitored parameter.

21. The method of claim 13 wherein selectively delivering RF energy from the one or more electrodes to renal nerves along the renal artery comprises thermally altering one or more renal nerves of the patient.

22. The method of claim 13 wherein selectively delivering RF energy from the one or more electrodes to renal nerves along the renal artery comprises ablating one or more renal nerves of the patient.

23. The method of claim 13 wherein selectively delivering RF energy from the one or more electrodes to renal nerves along the renal artery results in a reduction in renal sympathetic nerve activity of the hypertensive patient.

24. The method of claim 13 wherein at least partially blocking neural traffic to and/or from the kidney of the patient results in a therapeutically beneficial reduction in blood pressure of the hypertensive patient.

* * * * *